US012661077B2

(12) United States Patent
Shao et al.

(10) Patent No.: US 12,661,077 B2
(45) Date of Patent: Jun. 23, 2026

(54) MOBILE MEDICAL DEVICES

(71) Applicant: SHANGHAI UNITED IMAGING HEALTHCARE CO., LTD., Shanghai (CN)

(72) Inventors: Zhufeng Shao, Shanghai (CN); Junjie Miao, Shanghai (CN); Tao Huang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 18/814,627

(22) Filed: Aug. 26, 2024

(65) Prior Publication Data

US 2024/0415475 A1      Dec. 19, 2024

Related U.S. Application Data

(63) Continuation of application No. PCT/CN2023/085374, filed on Mar. 31, 2023.

(30) Foreign Application Priority Data

Mar. 31, 2022 (CN) .......................... 202220798811.0
Oct. 19, 2022 (CN) .......................... 202222757930.4

(51) Int. Cl.
*A61B 6/00* (2024.01)
*A61B 6/03* (2006.01)
*A61B 6/04* (2006.01)

(52) U.S. Cl.
CPC ............ *A61B 6/4405* (2013.01); *A61B 6/032* (2013.01); *A61B 6/0487* (2020.08)

(58) Field of Classification Search
CPC ........... A61B 6/10; A61B 6/102; A61B 6/105; A61B 6/4405; A61B 6/0487; A61B 6/56–566
See application file for complete search history.

(56) References Cited

U.S. PATENT DOCUMENTS

| | | |
|---|---|---|
| 2014/0037071 A1 | 2/2014 | Foerner et al. |
| 2014/0139215 A1 | 5/2014 | Gregerson et al. |
| 2018/0110494 A1 | 4/2018 | Hsieh |
| 2018/0184991 A1 | 7/2018 | Keertikumar |
| 2018/0184994 A1 | 7/2018 | Keertikumar |
| 2020/0245966 A1 | 8/2020 | I et al. |
| 2020/0405256 A1 | 12/2020 | Dickmann et al. |

FOREIGN PATENT DOCUMENTS

| | | |
|---|---|---|
| CN | 103083033 B | 10/2015 |
| CN | 210040744 U | 2/2020 |
| CN | 111588404 A | 8/2020 |
| CN | 112455246 A | 3/2021 |
| CN | 212879350 U | 4/2021 |

(Continued)

OTHER PUBLICATIONS

The Extended European Search Report in European Application No. 23778431.9 mailed on Mar. 31, 2025, 6 pages.

(Continued)

*Primary Examiner* — Carolyn A Pehlke
(74) *Attorney, Agent, or Firm* — METIS IP LLC

(57) ABSTRACT

The present disclosure provides mobile medical devices. The mobile medical device may include a main body. A gantry of the main body may be capable of moving.

20 Claims, 15 Drawing Sheets

(56)     References Cited

FOREIGN PATENT DOCUMENTS

| | | | |
|---|---|---|---|
| CN | 113456101 | A | 10/2021 |
| CN | 114077243 | A | 2/2022 |
| CN | 217244488 | U | 8/2022 |

OTHER PUBLICATIONS

International Search Report in PCT/CN2023/085374 mailed on Jul. 6, 2023, 5 pages.
Written Opinion in PCT/CN2023/085374 mailed on Jul. 6, 2023, 5 pages.

MOBILE MEDICAL DEVICES

CROSS-REFERENCE TO RELATED APPLICATIONS

This application is a Continuation of International Application No. PCT/CN2023/085374, filed on Mar. 31, 2023, which claims priority of Chinese Patent Application No. 202220798811.0, filed on Mar. 31, 2022, and Chinese Patent Application No. 202222757930.4, filed on Oct. 19, 2022, the entire contents of each of which are hereby incorporated by reference.

TECHNICAL FIELD

The present disclosure relates to the field of medical devices, and in particular, to mobile medical devices.

BACKGROUND

With the rapid development of the medical device industry, there is an increasing demand for the mobile medical device. This type of medical device has advantages such as high service efficiency, high environment utilization rate, flexible operation, etc., in application scenarios of multi-device collaborative diagnosis and treatment such as hybrid operating rooms, treatment rooms, etc.

SUMMARY

An aspect of the present disclosure provides mobile medical devices. The mobile medical device may include a main body. A gantry of the main body may be capable of moving.

In some embodiments, the mobile medical device may further include a base and a guide rail. The gantry of the main body may be movably disposed on the base and the gantry of the main body may be capable of moving along the guide rail.

In some embodiments, the mobile medical device may further include a first transmission component and a second transmission component. The second transmission component may be disposed on the gantry. The first transmission component and the second transmission component may be capable of being connected to transmit energy and/or a signal for the mobile medical device.

In some embodiments, the first transmission component may include a first connection terminal. The second transmission component may include a second connection terminal. The first connection terminal and the second connection terminal may coordinate to transmit the energy and/or the signal.

In some embodiments, the first connection terminal may be movably disposed. The first connection terminal may be connected to a first driving mechanism. The first driving mechanism may be configured to drive the first connection terminal to move.

In some embodiments, a driving power supply may be disposed on the gantry. The mobile medical device may include a second driving mechanism, and the second driving mechanism may be configured to drive the gantry to move. The driving power may be connected to the second driving mechanism.

In some embodiments, the driving power supply may be a rechargeable power supply and the driving power supply may be connected to the second connection terminal.

In some embodiments, a first electromagnet may be disposed on the first connection terminal and a second electromagnet may be disposed on the second connection terminal.

In some embodiments, the mobile medical device may further include an in-position detection mechanism.

In some embodiments, the first transmission component may include an electrical conductor extending along a movement direction of the gantry 121 of the main body 120. The second transmission component may include a power-taking device.

In some embodiments, the mobile medical device may further include an obstacle avoidance device and the obstacle avoidance device may include a contour detector. The contour detector may be configured to detect an obstacle in a moving direction of the main body according to a contour of the main body.

In some embodiments, the mobile medical device may further include a controller communicatively connected to the contour detector and the main body. The controller may be configured to: in response to that the contour detector detects that an obstacle exists in the moving direction of the main body, control the main body to brake to avoid the obstacle.

In some embodiments, the contour detector may include a front laser radar forming a detection area corresponding to the contour of the main body in front of the main body; and/or the contour detector may include a rear laser radar forming a detection area corresponding to the contour of the main body behind the main body.

In some embodiments, there may be a gap in the moving direction between the detection area and the main body. The detection area may cover a projection of the contour of the main body on the detection area along the moving direction.

In some embodiments, the contour detector may include at least two front laser radars, each of the at least two front laser radars may form a first detection sub-area in front of the main body, and the first detection sub-areas formed by the at least two front laser radars may be spliced into the detection area in front of the main body; and/or the contour detector may include at least two rear laser radars, each of the at least two rear laser radars may form a second detection sub-area behind the main body, and the second detection sub-areas formed by the at least two rear laser radars may be spliced into the detection area behind the main body.

In some embodiments, two front laser radars of the at least two front laser radars may be located on a left side and a right side of the main body, respectively, or located on an upper side and a lower side of the main body, respectively. In some embodiments, two rear laser radars of the at least two rear laser radars may be located on the left side and the right side of the main body, respectively, or located on the upper side and the lower side of the main body, respectively.

In some embodiments, the obstacle avoidance device may include an angle adjustment mechanism. The angle adjustment mechanism may adjust a tilt angle of the front laser radar and/or the rear laser radar based on a tilt angle of the main body.

In some embodiments, the main body may include a sliding table slidably mounted on the guide rail. The gantry may be disposed on the sliding table. The angle adjustment mechanism may include a mounting base rotatably disposed on the sliding table, a torsion spring disposed between the mounting base and the sliding table, an eccentric wheel against the mounting base, and a third driving mechanism drivably connected to the eccentric wheel. The front laser radar and/or the rear laser radar may be mounted on the mount. The third driving mechanism may drive the eccentric wheel to rotate and the mounting base may be biased by the eccentric wheel to adjust the tilt angle of the front laser radar and/or the rear laser radar mounted on the mounting base.

In some embodiments, the contour detector may be disposed on the main body and the contour detector may be driven by the main body to tilt and rotate synchronously.

In some embodiments, the front laser radar and the rear laser radar may include a two-dimensional laser radar or a three-dimensional laser radar.

In some embodiments, the contour detector may include a visual camera. A visual detection area of the visual camera may cover a moving area of the main body.

In some embodiments, the contour detector may detect a distance between the main body and the obstacle. The controller may be configured to: in response to a determination that the distance is smaller than or equal to a first preset distance, adopt a first obstacle avoidance strategy; or in response to a determination that the distance is greater than the first preset distance but smaller than or equal to a second preset distance, adopt a second obstacle avoidance strategy different from the first obstacle avoidance strategy, wherein the second preset distance is greater than the first preset distance.

In some embodiments, the first obstacle avoidance strategy may include controlling the main body to brake and stop. The second obstacle avoidance strategy may include controlling the main body to decelerate and/or controlling the contour detector to shorten a detection time interval.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, wherein.

DETAILED DESCRIPTION

Figure 1:
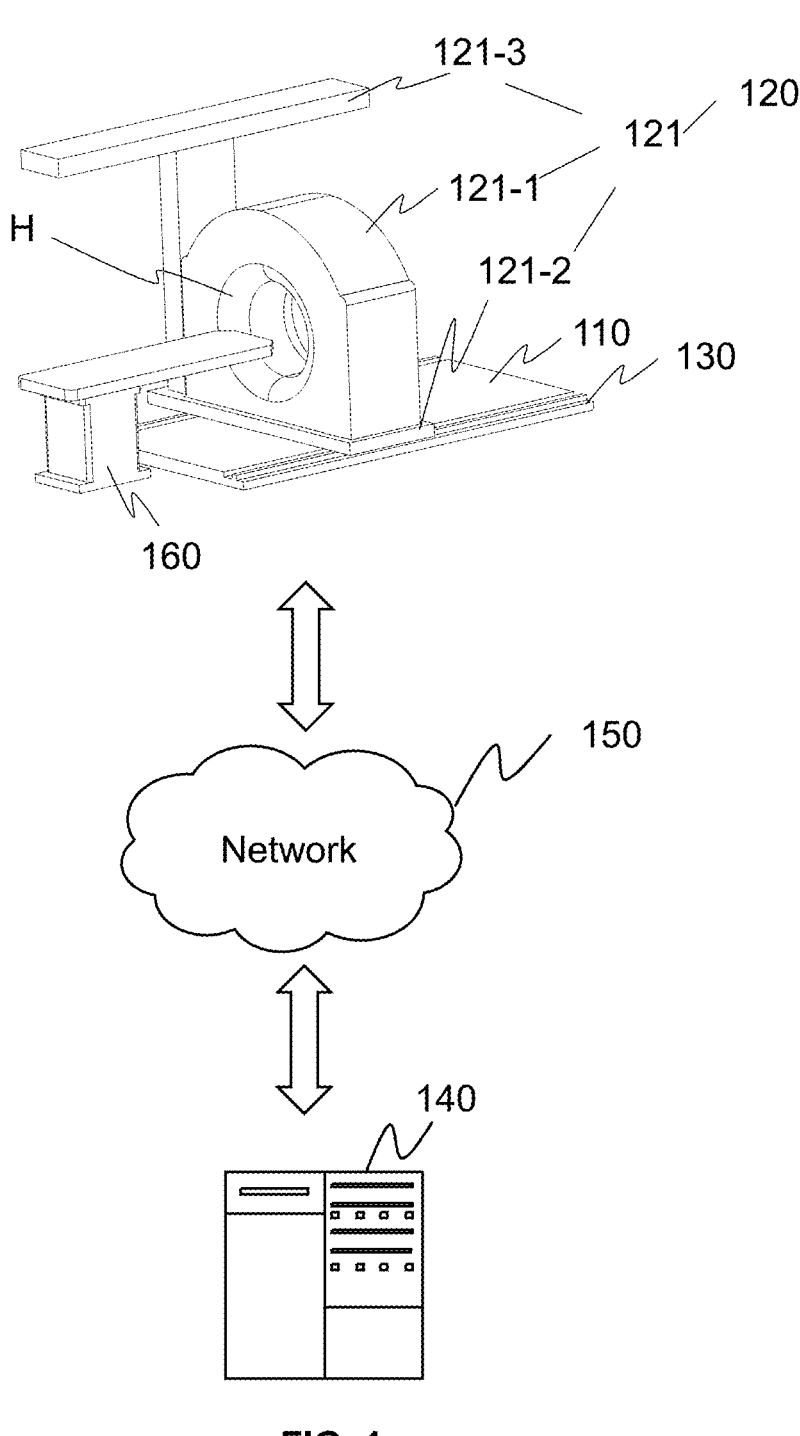
FIG. 1 is a schematic diagram illustrating an exemplary application scenario of a mobile medical device according to some embodiments of the present disclosure.

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words can achieve the same purpose, the words can be replaced by other expressions.

As used in the disclosure and the appended claims, the singular forms "a," "an," and "the" include plural referents unless the content clearly dictates otherwise; the plural forms may be intended to include singular forms as well. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

It should be understood that "install," "link," "connect," and "couple" should be understood in a broad sense, for example, connecting fixedly, connecting detachably, or connecting integrally; connecting mechanically or electrically; connecting directly, connecting indirectly through an intermediary, or connecting internally between two components. However, if other words can achieve the same purpose, the words can be replaced by other expressions.

FIG. 1 is a schematic diagram illustrating an exemplary application scenario of a mobile medical device 100 according to some embodiments of the present disclosure. In some embodiments, the mobile medical device 100 may include a main body 120. The main body 120 may include a gantry 121. In some embodiments, the gantry 121 of the main body 120 may be capable of moving. In some embodiments, the mobile medical device 100 may also include a processor 140. In some embodiments, the mobile medical device 100 may also include a network 150. In some embodiments, the mobile medical device 100 may further include a bed body 160.

The main body may include one or more types of devices capable of moving for medical operations. In some embodiments, the main body may include an imaging device capable of moving. In some embodiments, the main body may include a computed tomography (CT) device, a magnetic resonance scanning (MR) device, a digital radiography (DR) device, a positron emission tomography (PET) device, an ultrasonic device, a surgical robot, or the like, or any combination thereof.

The mobile medical device 100 may further include a base 110 and a guide rail 130. The gantry 121 of the main body 120 may be movably disposed on the base 110. The gantry 121 of the main body 120 may be capable of moving along the guide rail 130. In some embodiments, the gantry 121 of the main body 120 may be capable of moving by other means, for example, by providing a roller under the gantry 121. For ease of description, the following is illustrated by moving along the guide rail 130 as an example.

The base 110 refers to a component that carry the main body 120 (e.g., the gantry 121) and allow the gantry 121 to move.

The gantry 121 may be a support structure carrying one or more components of the main body 120. In some embodiments, the gantry 121 may be movably disposed on the base 110. In some embodiments, the gantry 121 may include a sliding table 121-2 slidably mounted on the guide table 130, a column 121-3 fixedly disposed on the sliding table 121-2, and a main body support part 121-1 disposed on the sliding table 121-2. The main body 120 may have a corresponding scanning hole H.

The guide rail 130 refers to a rail for the main body 120 (e.g., the gantry 121) to move. The guide rail 130 may play a role in guiding a movement direction of the gantry 121 of the main body 120.

The bed body 160 may be used to support a patient during surgery. For example, the bed body 160 may be used for a patient to lie on for CT scanning. In some embodiments, the bed body 160 may be disposed above the guide rail 130. The bed body 160 may be disposed corresponding to the scanning hole H. That is to say, the main body 120 may be moved to a position where the bed body 160 is located within the scanning hole H.

The processor 140 may directly issue program instructions or process data and/or information obtained from other devices or system components, so as to perform one or more functions described in the present disclosure. The processor 140 may execute the program instructions based on the data, information, and/or a processing result. For example, if the main body is a medical imaging device, the processor 140 may control the main body 120 to perform an imaging operation. As another example, the processor 140 may control the gantry 121 of the main body 120 to move. As yet another example, the processor 140 may obtain a distance between the gantry 121 and an obstacle and process the distance to obtain an obstacle avoidance strategy for avoiding friction and/or collision between the gantry 121 and the obstacle.

The network 150 may connect various components of the mobile medical device and/or connect the mobile medical device 100 with an external resource. The network 140 may enable communication between the various components and between the various components and other components outside the system, facilitating the exchange of data and/or information. For example, the network 150 may connect the processor 140 and the main body 120 to realize the control of the main body 120 by the processor 140 and realize the signal transmission between the processor 140 and the main body 120.

In some embodiments, the network 150 may include a wired network, a wireless network, or any combination thereof. For example, the network 150 may include a cable network, a fiber optic network, a telecommunications network, the Internet, a local area network (LAN), a wide area network (WAN), a wireless local area network (WLAN), a metropolitan area network (MAN), a public switched telephone network (PSTN), a Bluetooth network, a ZigBee network, a near field communication (NFC), a bus within the device, a line within the device, a cable connection, or the like, or any combination thereof. The mobile medical device involved in the embodiments of the present disclosure will be described in detail below with reference to FIGS. 2-15. It should be noted that the following embodiments are merely used to illustrate the present disclosure and not intended to constitute a limitation to the present disclosure.

Figure 2:
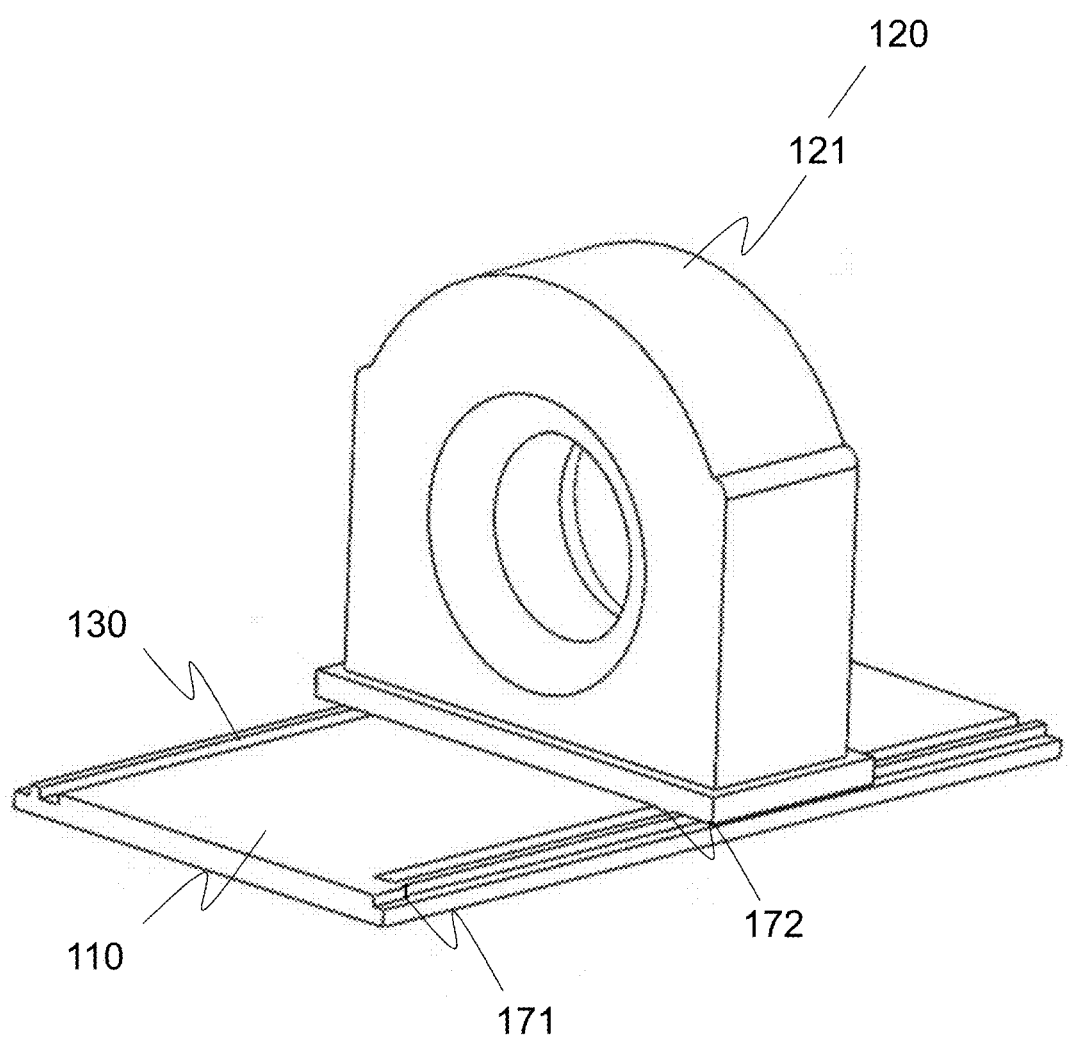
FIG. 2 is a schematic structural diagram illustrating a mobile medical device according to some embodiments of the present disclosure.

In some embodiments, as shown in FIG. 2, the mobile medical device may include a base 110, a main body 120, and a guide rail 130. The base 110 may be equipped with the guide rail 130. The main body 120 may include a gantry 121. The gantry may be movably disposed on the guide rail 130 and the gantry 121 may be capable of moving along the guide rail 130. It should be noted that the guide rail 130 may be a linear guide rail (as shown in FIG. 2), an arc guide rail, a circular guide rail, or guide rails of other shapes. In some embodiments, the guide rail 130 may be disposed on the base 110 (as shown in FIG. 2). In other embodiments, the guide rail 130 may be disposed elsewhere. For example, the guide rail 130 may be located on the ground below the base 110. As another example, the guide rail 130 may be located on the ceiling above the gantry 121. In some embodiments, rollers may be disposed on the gantry 121 and the rollers may roll along the guide rail 130, thereby driving the gantry 121 to move along the guide rail 130. In other embodiments, the gantry 121 may be equipped with a slider and the guide rail may include a chute for the slider to slide.

In some embodiments, the mobile medical device may further include a first transmission component and a second transmission component. The first transmission component may be disposed on the base 110 or may be disposed at other positions around the gantry 121, such as on the ground below the base 110, on the ceiling above the gantry 121, etc. The first transmission component may be connected to a power supply. The power supply may include an electric power, an emergency battery, etc., which may be used to supply power to the mobile medical device. In some embodiments, the first transmission component may be connected to a computer system that realizes a function such as controlling, imaging, etc. The second transmission component may be disposed on the gantry 121. The first transmission component may be electrically connected to the second transmission component. Transmission of energy and/or signal(s) may be performed for the medical device through the first transmission component and the second transmission component. For example, if the medical device includes a CT device and the CT device moves to a target position and performs scanning, the energy may be supplied to an X-ray tube of the CT device through the connection between the first transmission component and the second transmission component, and signal(s) associated with imaging data, control data, etc., may be transmitted during a scanning process of the CT device. The transmission of energy and/or signal(s) may be realized through the connection between the first transmission component and the second transmission component, which can avoid the use of cables, so that there is no need to drag the cables during the movement of the mobile medical device, thereby reducing interference and energy required for movement.

Figure 3:
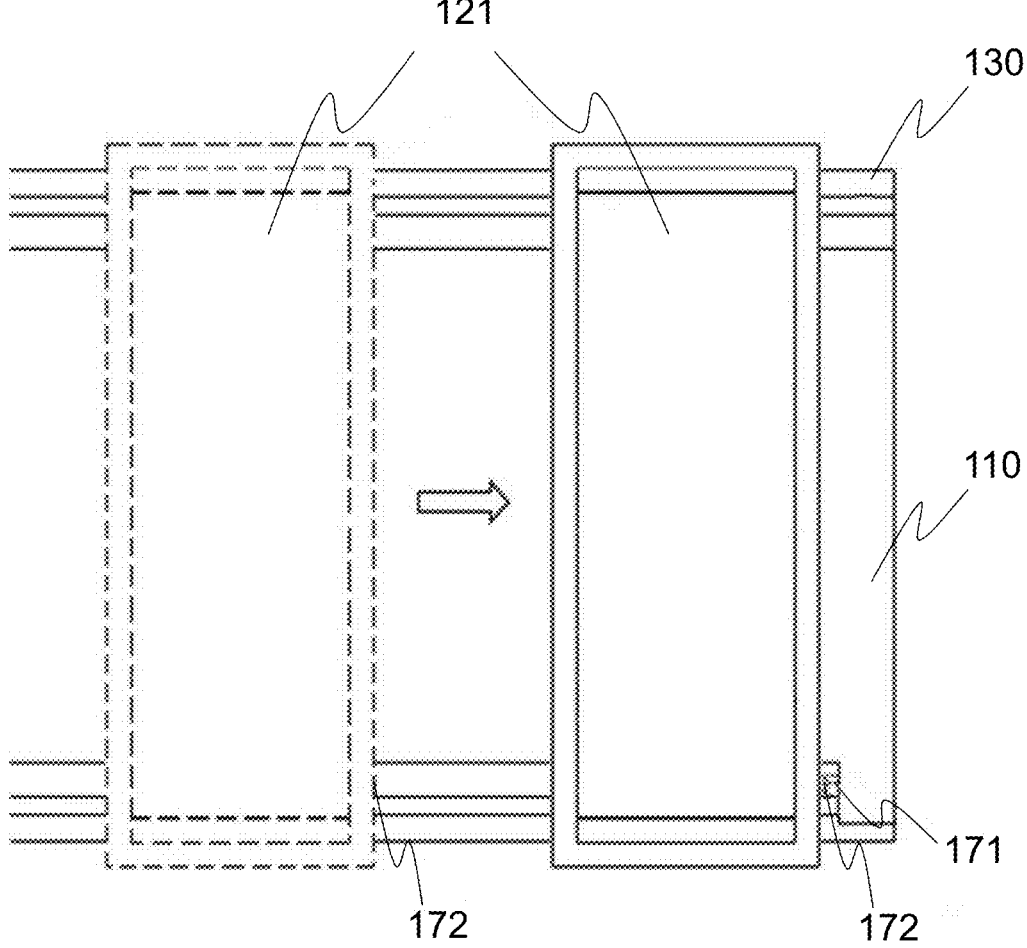
FIG. 3 is a schematic diagram illustrating movement of the mobile medical device according to some embodiments of the present disclosure.
Figure 4:
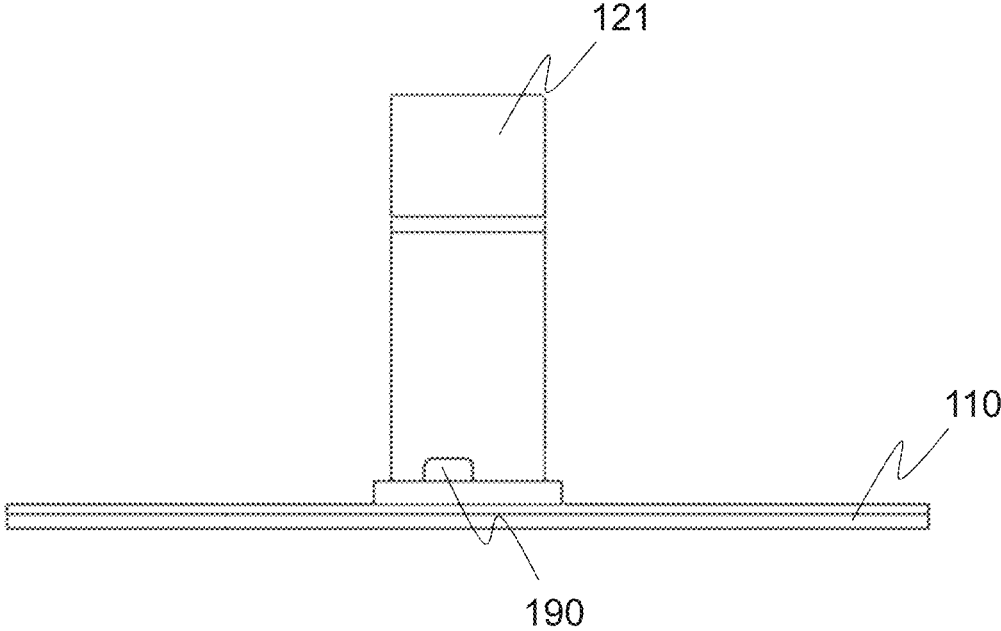
FIG. 4 is a side view illustrating a mobile medical device according to some embodiments of the present disclosure.

In some embodiments, as shown in FIGS. 2-4, the first transmission component may include a first connection terminal 171. Taking the guide rail 130 being a linear guide rail as an example, as shown in FIG. 2, the first connection terminal 171 may be mounted on the base 110 and may be located at one end of the guide rail 130. The first connection terminal 171 may be connected to the power supply and/or the computer system for controlling and imaging through an internal cable inside the base 110. In some embodiments, the first connection terminal 171 may be mounted at a position (e.g., ground, wall) that is in contact with the second connection terminal 172 to achieve electrical connection, which is not limited herein. The second transmission component may include a second connection terminal 172. The second connection terminal 172 may be fixedly disposed at one end of the gantry 121. When moving along the guide rail 130, the gantry 121 may drive the second connection terminal 172 to move. When the gantry 121 moves to one end of the guide rail 130, the first connection terminal 171 may contact the second connection terminal 172 to realize electrical connection, so as to realize energy supply and/or signal transmission for the mobile medical device. In some embodiments, if the guide rail 130 is a non-linear guide rail (e.g., a circular guide rail), the first connection terminal 171 may be disposed at a preset position of the circular guide rail, and the preset position may be determined according to a target position of the scanning of the medical device.

In some embodiments, the first transmission component and the second transmission component may be wirelessly energized to achieve energy supply and/or signal transmission for medical treatment. A first induction coil may be installed in the first connection terminal 171, and the first induction coil may be connected to a power supply as a power supply terminal. A second induction coil may be installed in the second connection terminal 172 as a power-taking terminal. If the first connection terminal 171 is connected to the second connection terminal 172, the first induction coil and may be close to the second induction coil, and a certain current may be generated in the second induction coil to transfer electric energy from a transmitting terminal (e.g., the first connection terminal 171) to a receiving terminal (e.g., the second connection terminal 172), so as to supply power from the power supply terminal to the power-taking terminal. When the first connection terminal 171 is separated from the second connection terminal 172, the first induction coil may be far away from the second induction coil, no current may be generated in the second induction coil, and no power may be supplied from the power supply terminal to the current-using terminal.

In some embodiments, the first connection terminal 171 may have an external cable exposed outside the base 110. The external cable may be connected to an internal cable inside the base 110. The first connection terminal 171 may be connected to the power supply and/or the computer system that realize a function such as controlling, imaging, etc., through the external cable and/or the internal cable. When the gantry 121 moves along a direction guided by the guide rail 130 (the guiding direction may be a straight line, an arc, a circle, etc.), for example, when the medical device needs to operate on a plurality of parts of the patient, the gantry 121 may need to stop at a plurality of different positions. If the gantry 121 stops at the required position and there is still a certain distance between the first connection terminal 171 and the second connection terminal 172, the external cable of the first connection terminal 171 may be manually/automatically pulled out to connect the second connection terminal 172 to the first connection terminal 171.

In some embodiments, the first connection terminal 171 may be movably disposed (e.g., disposed on the base). The first connection terminal 171 may be connected to a first driving mechanism (not shown in the figure). The first driving mechanism may be configured to drive the first connection terminal 171 to move (e.g., move along the guide rail). In some embodiments, the first connection terminal 171 may slide within a certain length range. In some embodiments, a movable length range of the first connection terminal 171 may be smaller than that of the second connection terminal 172. That is to say, the first connection terminal 171 may be connected to the cable to move within a small range. In this way, it may only need to drag the cable of the first connection terminal 171 within the small range. In other embodiments, the first connection terminal 171 may include a current collector disposed on a strip-shaped electrical conductor and the strip-shaped electrical conductor may extend along an extension direction of the guide rail. The strip-shaped electrical conductor may be connected to the power supply and/or the computer system that realize a function such as controlling, imaging, etc. With such an arrangement, the first connection terminal 171 and the gantry 121 (on which the second connection terminal 172 is disposed) may move in cooperation with each other, so as to realize the connection between the first transmission component and the second transmission component.

In some embodiments, the first driving mechanism may include a driving member and a transmission mechanism connected to the driving member. In some embodiments, the driving member may include a motor, a hydraulic cylinder, a pneumatic cylinder, etc. In some embodiments, the first driving mechanism may be a linear motor, a rotary motor, or the like. The driving member may be connected to the driving power supply 190 and the transmission mechanism may be connected to the driving member. The transmission mechanism may include a rack-and-pinion transmission mechanism, a worm-and-gear transmission mechanism, a belt transmission mechanism, etc.

In some embodiments, as shown in FIG. 4, a driving power supply 190 for driving the gantry 121 to move may be disposed on the gantry 121. The driving power supply 190 may be a rechargeable power supply. The main body 120 may include a second driving mechanism (not shown in the figure) and the driving power supply 190 may be connected to the second driving mechanism. The second driving mechanism may be configured to drive the gantry 121 to move (e.g., move along the guide rail 130). For example, when the medical device includes a CT device, in a process of moving the gantry 121 of the CT device to a target position, the required energy may be small since the CT device does not need to perform scanning when moving. Therefore, the gantry 121 may be provided with the energy required for the movement by the driving power supply 190 carried by the gantry 121. In some embodiments, the driving power supply 190 may be detachably connected to the gantry 121. When the power of the driving power supply 190 is insufficient, the driving power supply 190 may be removed for charging without using charging cables.

In some embodiments, the mobile medical device may include a power monitoring mechanism connected to the driving power supply 190. When the power of the driving power supply 190 is less than a preset value, the power monitoring mechanism may sound an alarm to remind an operator to charge in time. In some embodiments, the driving power supply 190 may be a non-rechargeable power supply, such as a carbon battery, an alkaline battery, etc.

In some embodiments, the second driving mechanism may be configured similarly to the first driving mechanism. In other embodiments, the gantry 121 may be pulled by an external pulling device to move on the guide rail 130.

In some embodiments, the driving power supply 190 may be connected to the second connection terminal 172. For example, if the medical device includes the CT device and the gantry 121 of the CT device moves to the target position to enable the first connection terminal 171 to contact the second connection terminal 172 (at this time, scanning may be performed), the second connection terminal 172 on the gantry 121 may be automatically aligned and plugged with the first connection terminal 171 fixed on the base 110, so that not only stable supply of large energy may be realized during the scanning, but also the first connection terminal 171 and the second connection terminal 172 may synchronously charge the driving power supply 190 carried by the gantry 121, thereby ensuring the stability of the driving power supply 190.

In some embodiments, the mobile medical device may further include a first controller and a position sensor (not shown in the figure) and the position sensor may be connected to the first controller. The first controller may be a part of the processor 140. The first controller and the processor 140 may be two independent components. When the first connection terminal 171 is fixed on the base, the position sensor may detect a real-time position of the gantry 121 and the first controller may control, based on the position, the second driving mechanism (not shown in the figure) to drive the gantry 121 to move to a target position (e.g., move to a target position along the guide rail 130), so that the driving power supply 190 may be charged. The target position may be a position where the medical device performs the scanning and/or a position where the first connection terminal 171 and the second connection terminal 172 can be connected.

When the first connection terminal 171 is slidably disposed on the base 110, the position sensor may be used to detect a position of the gantry 120 and a real-time position of the first connection terminal 171. Accordingly, the first controller may control the first driving mechanism to drive the first connection terminal 171 based on the position of the gantry 121 and the position of the first connection terminal 171 and/or the second driving mechanism to drive the gantry 121 to move to the target position (e.g., move to the target position along the guide rail 130) so that the driving power supply 190 may be charged.

In some embodiments, in response to that the first controller detects that the power of the driving power supply 190 is less than the preset value or level (e.g., 5% of full power, 10% of full power, 20% of full power, etc.), the first controller may control the first driving mechanism to drive the first connection terminal 171 and/or the second driving mechanism to drive the gantry 121 to move to the target position (e.g., move to the target position along the guide rail 130) and to charge the driving power supply 190.

Figure 5:
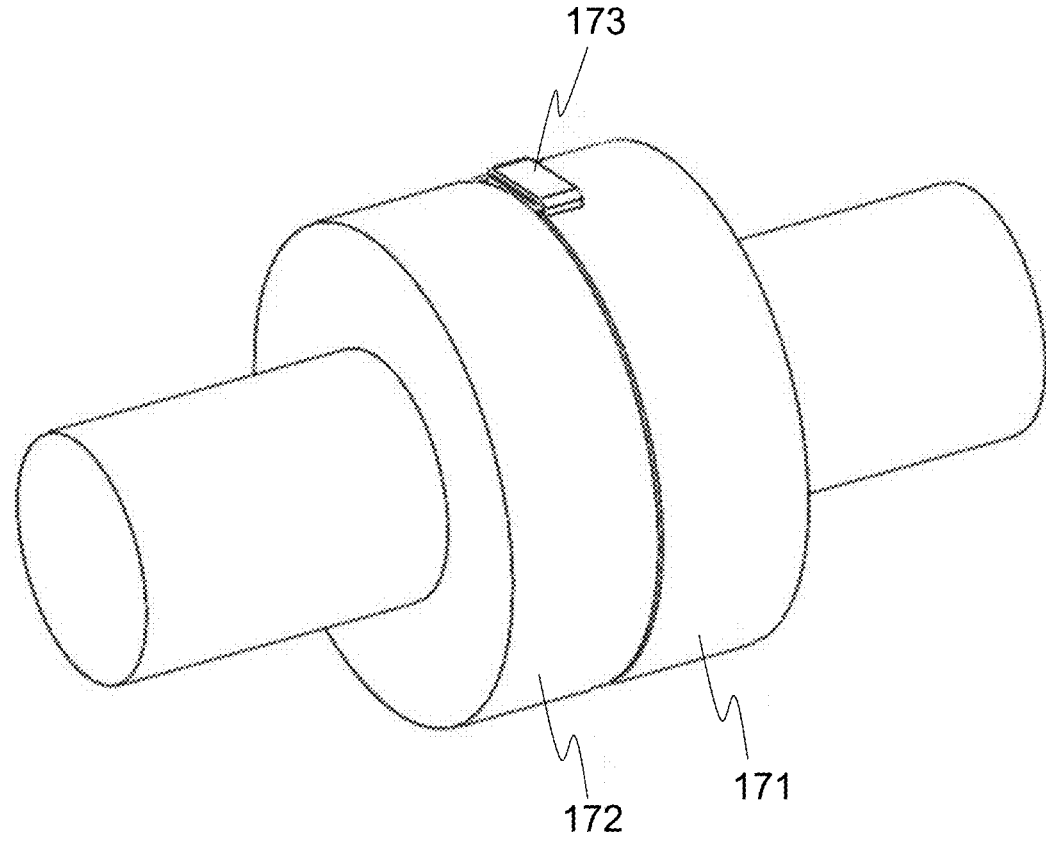
FIG. 5 is a schematic diagram illustrating a first transmission component and a second transmission component of a cable according to some embodiments of the present disclosure.

In some embodiments, when the gantry 121 moves (e.g., move along the guide rail 130) and the first transmission component and the second transmission component are close together, the first connection terminal 171 and the second connection terminal 172 may be automatically plugged in and connected through an aligning and plugging-in structure, thereby realizing quick alignment of the first connection terminal 171 and the second connection terminal 172 to transmit energy and/or a signal for the mobile medical device. In some embodiments, as shown in FIG. 5, the second connection terminal 172 on the gantry 121 and the first connection terminal 171 on the base 110 may achieve stable contact through magnetic attraction. In some embodiments, the aligning and plugging-in structure may include a first electromagnet disposed on the first connection terminal 171 and a second electromagnet disposed on the second connection terminal 172. When the gantry 121 moves to the target position so that the first connection terminal 171 can contact the second connection terminal 172, the first electromagnet and the second electromagnet may be energized to generate magnetic attraction, so as to realize the automatic alignment and plugging-in of the second connection terminal 172 and the first connection terminal 171 and ensure that the second connection terminal 172 and the first connection terminal 171 are capable of remaining connected and contacted. When the scanning is completed, the first electromagnet on the first connection terminal 171 and the second electromagnet on the second connection terminal 172 may be powered off and lose a magnetic force and the movement of the gantry 121 may drive the second connection terminal 172 to break away from the first connection terminal 171 quickly. In some embodiments, the aligning and plugging-in structure may include a guide bump disposed on one of the first connection terminal 171 and the second connection terminal 172 and a groove disposed on the other of the first connection terminal 171 and the second connection terminal 172. The guide bump may be matched with the groove, so that the guide bump may be plugged into the groove. When close to each other, the first connection terminal 171 and the second connection terminal 172 may be quickly aligned through the plugging-in of the guide bump and the groove.

In some embodiments, as shown in FIG. 5, the mobile medical device may further include an in-position detection mechanism 173. The in-position detection mechanism 173 may be used to detect whether the second connection terminal 172 and the first connection terminal 171 are correctly connected. In some embodiments, the in-position detection mechanism 173 may detect whether an internal switch is triggered to achieve the in-position detection, so as to determine whether the second connection terminal 172 and the first connection terminal 171 are connected correctly. In some embodiments, the in-position detection mechanism 173 may detect whether the second connection terminal 172 and the first connection terminal 171 are connected correctly by detecting high-low transformation of an electrical level within the base 110. In some embodiments, when the in-position detection mechanism 173 detects that the second connection terminal 172 and the first connection terminal 171 are correctly connected, the medical device, may start to work again (e.g., perform scanning).

Figure 6:
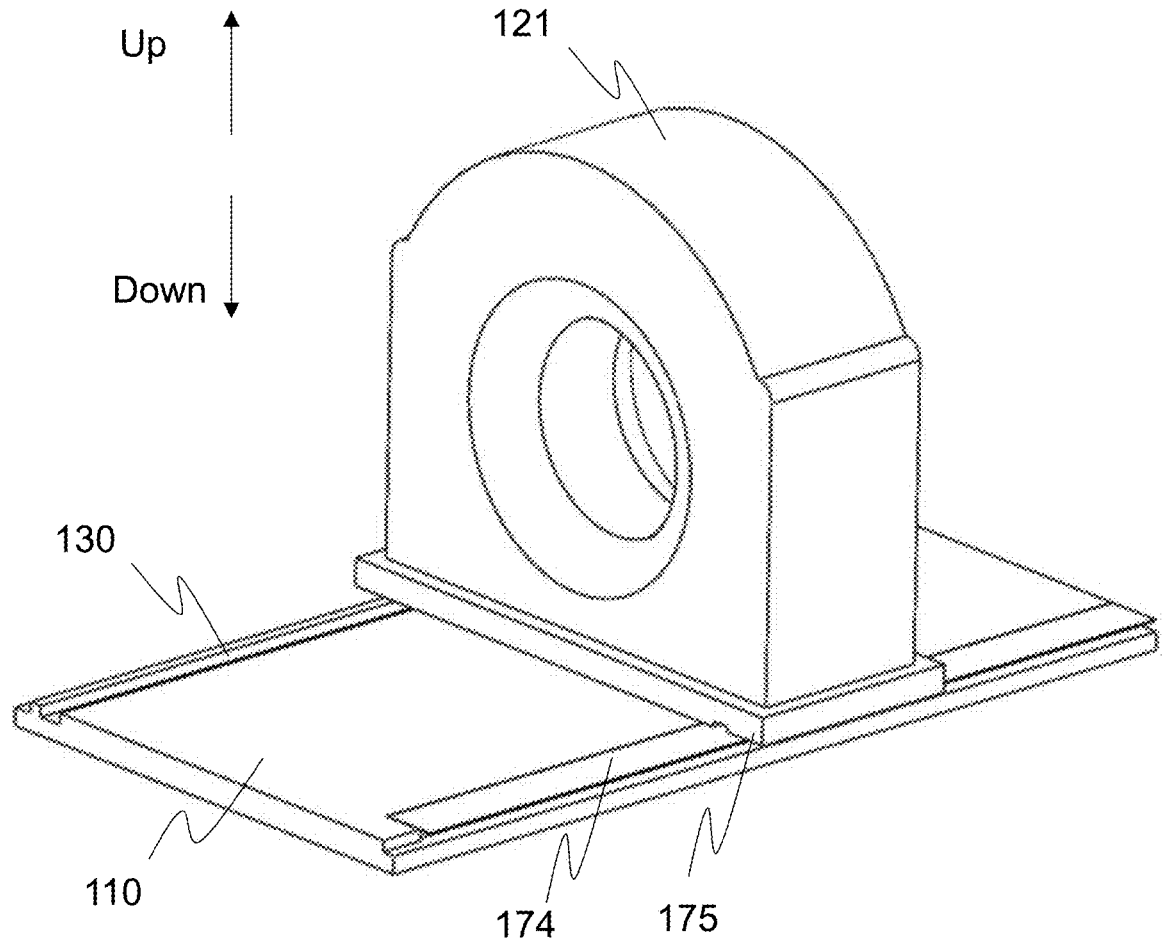
FIG. 6 is a schematic structural diagram illustrating a mobile medical device according to another embodiment of the present disclosure.

In some embodiments, as shown in FIG. 6, the first transmission component may include an electrical conductor 174 extending along a movement direction of the gantry 121 of main body 120. The electrical conductors 174 may be connected to the power supply and the computer system that realize a function such as controlling and/or imaging. In some embodiments, the electrical conductor 174 may include one or more strip-shaped electrical conductors, one or more plate-shaped electrical conductors, etc. The second transmission component may include a power-taking device 175 mounted on the gantry 121. When the gantry 121 moves along the guide rail 130, the power-taking device 175 may be keep in contact with the electrical conductor 174 and the electrical conductor 174 and the power-taking device 175 may realize the transmission of energy and/or signal(s) for the mobile medical device through the cooperation of the electrical conductor 174 and the power-taking device 175 no matter where the gantry 121 moves on the guide rail 130. For example, when the mobile medical device includes a CT device, the CT device may stop at any position of the guide rail 130, perform the scanning, supply an X-ray tube of the CT device with energy at any position through the contact of the electrical conductor 174 and the power-taking device 175, and also transmit a signal such as imaging data, control data, etc., during the scanning process of the X-ray tube.

In some embodiments, the power-taking device 175 may be connected to the second driving mechanism. The movable gantry 121 may need to constantly change a position due to the movement. At each position, the second driving mechanism may obtain the energy to drive the gantry 121 to move at any time. Merely by way of example, when the gantry 121 moves, the power-taking device 175 may operate synchronously with the gantry 121 and obtain energy from the electrical conductor 174 at any time to provide the energy to the second driving mechanism within the gantry 121, so that the gantry 121 may continue to move. That is to say, through the contact of the electrical conductor 174 and the power-taking device 175, energy transmission (e.g., power supply) and/or signal transmission (e.g., a signal for moving a position) may be realized during the movement of the gantry. In other embodiments, when the first transmission component includes the electrical conductor 174 and the second transmission component includes the power-taking device 175, the second driving mechanism may be powered by the driving power supply 190. In some embodiments, if the first transmission component includes the electrical conductor 174 and the second transmission component includes the power-taking device 175, the gantry 121 may be pulled by an external pulling device to move on the guide rail 130.

In some embodiments, as shown in FIG. 6, the electrical conductor 174 may be disposed on the base 110 on a same plane as the guide rail 130 and parallel to the guide rail 130. In such cases, the electrical conductor 174 may be used not only as a charging device, but also as an auxiliary guide rail, so that the whole device may have a compact structure and occupation of the space of an operating room may be reduced. In some embodiments, the electrical conductor 174 may also be disposed under the base 110 and the corresponding power-taking device 175 may be disposed at the bottom of the gantry 121. For example, the electrical conductor 174 may be fixedly disposed on the ground where the mobile medical device is placed. If the electrical conductor 174 is directly laid on the ground, a power supply cable connected to the electrical conductor 174 may be hidden under the ground, thereby avoiding fetters of the wired cable to a greatest extent. In some embodiments, the electrical conductor 174 may be disposed above the gantry 121 and the corresponding power-taking device 175 may be disposed on the top of the gantry 121. For example, the electrical conductor 174 may be suspended on a roof. In such cases, the wired cable may be located in the upper space of the operating room, which may not affect operator's walking and device operation.

Figure 7:
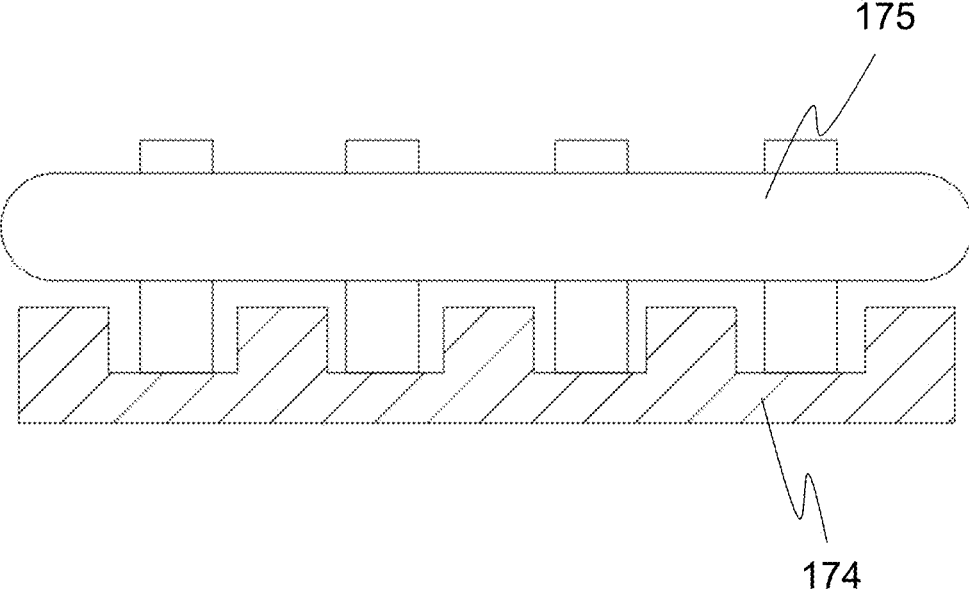
FIG. 7 is a structural schematic diagram illustrating an electrical conductor cooperating with a power-taking device of a mobile medical device according to some embodiments of the present disclosure.

In some embodiments, the power-taking device 175 may include a current collector. For example, as shown in FIG. 7, the power-taking device 175 may include a brush type current collector.

In some embodiments, the mobile medical device may further include a locking mechanism disposed between the base 110 and the gantry 121. When the medical device is used, the gantry 121 may move to a target position according to an actual need and start to work. In order to improve the working effect (e.g., improving imaging quality of the CT device), a relative position of the gantry 121 and the base 110 may need to be locked. The locking mechanism may be used to connect the gantry 121 to the base 110 fixedly, so that the relative position of the gantry 121 and the base 110 may be locked. The locking mechanism may include a mechanical manual locking mechanism (e.g., a fastening bolt, latch, etc.) or an automatic locking mechanism (e.g., an electrical locking mechanism). For example, the locking mechanism may be the fastening bolt mounted on the gantry 121. Fastening screw may pass through both sides of the gantry 121 and a lower end of the fastening screw may abut against the base 110. When the gantry 121 needs to be moved, the fastening bolt may be in a loose state. When the gantry 121 moves to a desired designated position and the gantry 121 needs to be fixed, the locking of the relative position of the gantry 121 and the base 110 may be achieved by tightening the fastening screw. As another example, the locking mechanism may also be an electromagnetic locking mechanism mounted on the gantry 121. The electromagnetic locking mechanism may include a first electromagnetic block and a second electromagnetic block. The first electromagnetic block may be disposed on the gantry 121 and the second electromagnetic block may be disposed on the base 110. Both the first electromagnetic block and the second electromagnetic block may be strip-shaped and parallel to a moving direction of the gantry 121. When the gantry 121 needs to be moved and the electromagnetic locking mechanism is not energized, there may be no magnetic attraction force between the first electromagnetic block and the second electromagnetic block. When the rack 121 moves to the desired or designated position and needs to be fixed and the electromagnetic locking mechanism is energized, the magnetic attraction force may be generated between the first electromagnetic block and the second electromagnetic block and the gantry 121 and the base 110 may be attracted to each other under the action of the magnetic attraction force, so that the relative positions of the gantry 121 and the base 110 may be locked.

According to some embodiments of the present disclosure, the medical device does not need to be bound by the cable during the movement and the movement of the medical device is more flexible, so that the medical device may not need to provide additional power to drag the heavy cable to move when moving, the energy consumption caused by dragging the cable and management and maintenance of the cable may be reduced, and the occupation of the space of the operating room may be reduced. When the medical device moves to the target position, the first transmission component and the second transmission component may realize the stable transmission of energy and/or signal(s) for the medical device to ensure the normal operation of the medical device (for example, to ensure that the CT device performs normal scanning).

Considering that in application scenarios of multi-device collaborative diagnosis and treatment, such as in operating rooms or treatment rooms, the medical device may need to move frequently on the rail and an obstacle may be likely to appear on a moving route of the medical device. In such cases, if a position of the obstacle cannot be detected and judged in time, there may be a risk of direct contact and collision with the obstacle, which may lead to a medical accident in a severe case.

Figure 8:
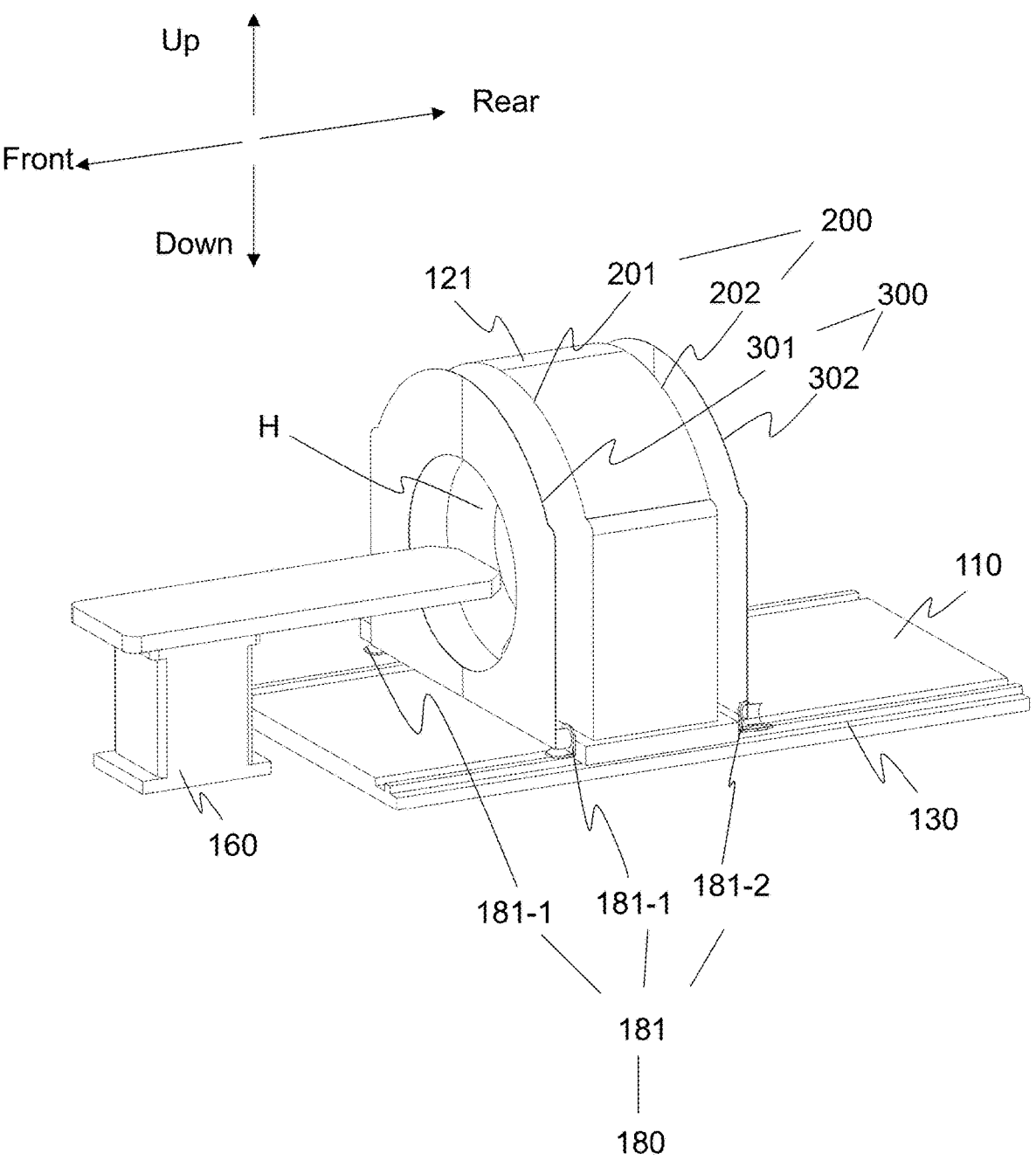
FIG. 8 is a schematic diagram illustrating obstacle avoidance detection of a mobile medical device according to some embodiments of the present disclosure.

In some embodiments, as shown in FIG. 8, the mobile medical device may include an obstacle avoidance device and the obstacle avoidance device may include a contour detector 180. The contour detector 180 may be used to detect the obstacle in a moving direction of the main body 120 (e.g., along the guide rail 130) according to a contour of the main body 120. The contour detector 180 may detect the obstacle in the moving direction of the main body 120 according to the contour of the main body 120, so as to prompt an operator or provide a basis for an obstacle avoidance operation of the mobile medical device 100. In addition, the contour detector 180 may only detect the obstacle (e.g., an obstacle that may collide with the contour) corresponding to the contour of the main body 120 in the moving direction and not detect other obstacles (e.g., an obstacle that may not collide with the contour) that are not related to the contour, so as to effectively avoid a false alarm and ensure that the mobile medical device has high CT scanning efficiency while having a timely obstacle avoidance function.

In some embodiments, the mobile medical device may include a reminder mechanism. The reminder mechanism may be connected to the contour detector 180. When the contour detector 180 detects that the obstacle exists in the moving direction of the main body 120, the reminder mechanism may remind the operator. In some embodiments, the reminder mechanism may include a speaker and/or a display screen, etc. A corresponding reminder method of the reminder mechanism may include voice broadcast and/or screen flashing, etc.

In some embodiments, the mobile medical device may include a controller (i.e., a second controller). The second controller and the first controller be a same controller or different controllers. The second controller may be a part of the processor 140. Alternatively, the second controller and the processor 140 may be two independent components. The second controller may be used to be communicatively connected to the contour detector 180 and the main body 120 (e.g., the second driving mechanism of the main body 120). When the contour detector 180 detects that the obstacle in the moving direction of the main body 120, the second controller may control the main body 120 (e.g., the second driving mechanism of the main body 120) to brake to avoid the obstacle, thereby reducing occurrence of a collision and a medical accident.

The second controller may control the main body 120 to brake to avoid the obstacle when the contour detector 180 detects that there is an obstacle. Therefore, the mobile medical device in the embodiments of the present disclosure can not only avoid the obstacle in time, reduce or eliminate the occurrence of the collision and the medical accident, and thus, false alarm may be prevented, and normal scanning operation of the main body 120 may not be affected by the false alarm.

In some embodiments, as shown in FIG. 8, the contour detector 180 may include a front laser radar 181-1 having a detection area 300 corresponding to a contour 200 of the main body in front of the main body 120. In some embodiments, the contour detector 180 may include a rear laser radar 181-2 having the detection area 300 corresponding to the contour 200 of the main body behind the main body 120. The detection area 300 refers to an area detected by the laser radar 181. When the obstacle enters the detection area 300, the contour detector 180 may identify the obstacle. The detection area 300 may be a two-dimensional planar area or a three-dimensional spatial area, depending on a specific type of the contour detector 180. The detection area 300 corresponding to the contour of the main body 120 may be referred to that the detection area 300 is generated based on the contour of the main body 120 and the detection area 300 reflects a feature of the contour of the main body 120. For example, the detection area 300 may cover a projection of the contour 200 of the main body on the detection area 300 along the moving direction. As another example, the detection area 300 may have a same shape as the contour of the main body 120 and the detection area 300 may be slightly larger than the contour 200 of the main body. In addition, the detection area 300 may be an area where the contour of the main body 120 is about to reach after moving along the moving direction for a certain period of time. If the laser radar 181 detects that the obstacle exists in the detection area 300, it may mean that the contour of the main body 120 will collide with the obstacle after moving along the moving direction for a certain period of time.

In some embodiments, the contour 200 of the main body may refer to an outer contour of the main body 120. In some embodiments, the contour 200 of the main body may refer to an area between an inner contour and the outer contour of the main body 120. For example, as shown in FIG. 8, if the mobile medical device includes a bed body 160, the main body 120 may include a scanning hole H corresponding to the bed body 160, so that when the gantry 121 moves back and forth along the guide rail 130, the bed body 160 may enter and exit the scanning hole H, so as to scan the body of the patient lying thereon. At this time, the contour 200 of the main body may refer to the area between the outer contour of the main body 120 and the inner contour of the main body 120. The outer contour of the main body 120 refers to an outer edge of a housing of the main body 120. The inner contour of the main body 120 refers to an outer edge of the scanning hole H.

The contour of the main body may include a front contour area 201 and a rear contour area 202. Correspondingly, the detection area 300 may include a front detection area 301 corresponding to the front contour area 201 and a rear detection area 302 corresponding to the rear contour area 202. When the main body 120 moves forward along the guide rail 130, it may be only necessary to detect whether there is an obstacle in the front detection area 301 corresponding to the front contour area 201 of the main body 120. Similarly, when the main body 120 moves backward along the guide rail 130, it may be only necessary to detect whether there is an obstacle in the rear detection area 302 corresponding to the rear contour area 202 of the main body 120.

The contour detector 180 may not only detect the obstacle in the moving direction of the main body 120 according to the contour of the main body 120, but also may detect whether the body of the patient lying on the bed body 160 exceeds the scanning hole H, so as to prevent the main body 120 from colliding with the body (e.g., a head, a trunk, limbs, etc.) of the patient during movement, thereby avoiding collision injuries to the patient and improving the safety performance of the mobile medical device.

In some embodiments, the front laser radar 181-1 may include a two-dimensional laser radar. In some embodiments, the rear laser radar 181-2 may include a two-dimensional laser radar. In some embodiments, the front laser radar 181-1 may include a three-dimensional laser radar. In some embodiments, the rear laser radar 181-2 may include a three-dimensional laser radar. The two-dimensional laser radar may use a pulse time-of-flight principle in detection. The laser pulse may be continuously emitted by the two-dimensional laser radar and the laser pulse may be emitted by a rotating optical mechanism at a certain angular interval (e.g., an angular resolution) to each direction within the scanning angle to form a two-dimensional scanning surface based on radial coordinates. Three-dimensional laser radar may be used to achieve measurement of three-dimensional coordinates in space by rotating a gimbal and the two-dimensional laser radar. The two-dimensional laser radar may form a two-dimensional scanning surface and the two-dimensional scanning surface may be rotated through the gimbal to form a three-dimensional point cloud in space. The three-dimensional laser radar may form a three-dimensional detection area 300. The three-dimensional laser radar may further realize distance detection between the main body 120 and the obstacle. The three-dimensional laser radar may realize contour detection and distance detection at the same time with high detection accuracy. In some embodiments, the obstacle avoidance device may include a distance sensor. In some embodiments, the distance sensor may cooperate with the two-dimensional laser radar to realize both the contour detection and the distance detection and improve the detection accuracy.

In some embodiments, a count of the front laser radars 181-1 may be the same as or different from a count of the rear laser radars 181-2. For example, there may be two front laser radars 181-1 and three rear laser radars 181-2. In some embodiments, a type of the front laser radar 181-1 may be the same as or different from a type of the rear laser radar 181-2. For example, the front laser radar 181-1 may be a two-dimensional laser radar and the rear laser radar 181-2 may be a three-dimensional laser radar. In some embodiments, the counts and the types of the front laser radar 181-1 and the rear laser radar 181-2 may be determined based on the contour 200 of the main body. For example, if the front contour area 201 is a two-dimensional plane, the front laser radar 181-1 may be a two-dimensional laser radar.

In some embodiments, the front laser radar 181-1 may form the front detection area 301 corresponding to the contour 200 of the main body in front of the main body 120 by emitting laser light, so as to scan and detect whether there is an obstacle in the front detection area 301. In some embodiments, the rear laser radar 181-2 may form the rear detection area 302 corresponding to the contour 200 of the main body behind the main body 120 by emitting laser light, so as to scan and detect whether there is an obstacle in the rear detection area 302.

In some embodiments, as shown in FIG. 8, there may be a gap in the moving direction between the detection area 300 and the main body 120 and the detection area 300 may cover a projection of the contour 200 of the main body on the detection area along the moving direction. For example, there may be the gap in the moving direction between the front detection area 301 and the front contour area 201.

When the front laser radar 181-1 detects that there is the obstacle in the front detection area 301, the second controller may control the main body 120 to brake to avoid the obstacle, so that the main body 120 may be braked to stop in time and sufficient avoidance space may be reserved to prevent friction and collision between the main body 120 and the obstacle. As another example, as shown in FIG. 8, if the front contour area 201 is a plane, the front detection area 301 may be parallel to the front contour area 201 of the main body 120, there may be a gap between the front detection area 301 and the front contour area 201 in the moving direction, and the front detection area 301 may cover a projection of the front contour area 201 on the front detection area 301 along the moving direction. The detection area 300 may cover the projection of the contour 200 of the main body on the detection area along the moving direction, which can ensure that the obstacle outside the detection area 300 will not collide with the main body 120.

Figure 11:
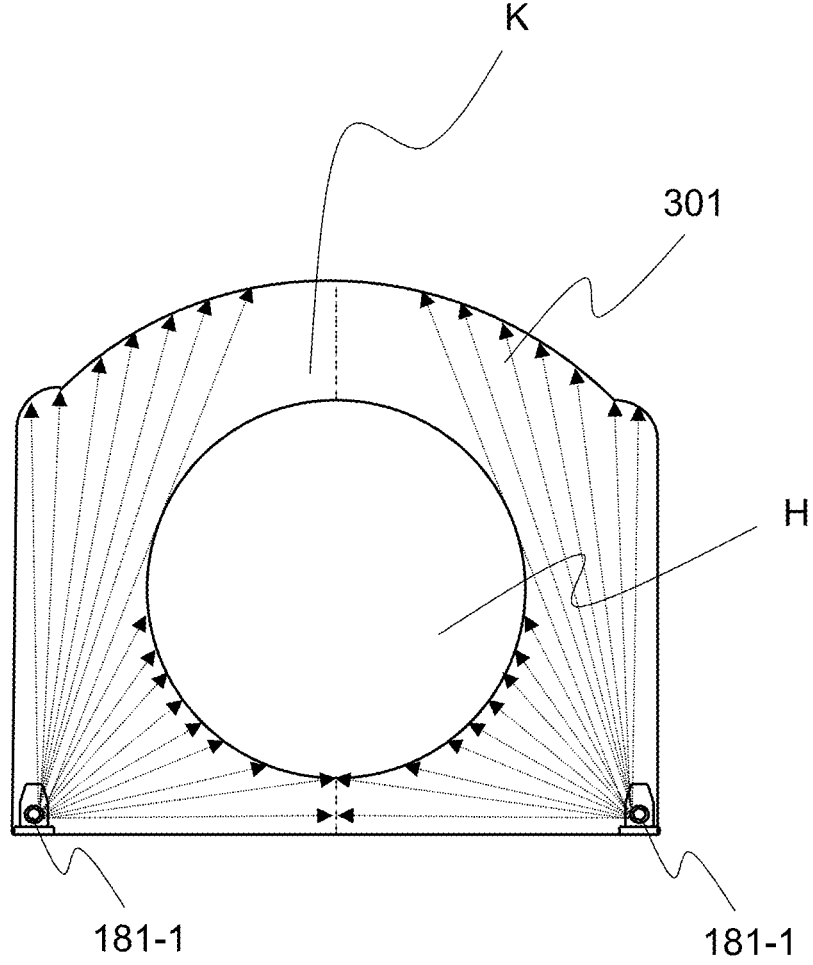
FIG. 11 is a schematic diagram illustrating a front detection plane of a front laser radar according to some embodiments of the present disclosure.

In some embodiments, the contour detector 180 may include at least two front laser radars 181-1. Each of the at least two front laser radars 181-1 may have a first detection sub-area in front of the main body. The first detection sub-areas of the at least two front laser radars 181-1 may be spliced into the front detection area 301 in front of the main body 120. In some embodiments, the contour detector 180 may include at least two rear laser radars 181-2. Each of the at least two rear laser radars 181-2 may have a second detection sub-area behind the main body. The second detection sub-areas of the at least two rear laser radars 181-2 may be spliced into the rear detection area 302 behind the main body 120. As shown in FIG. 11, the first detection sub-areas of the two front laser radars 181-1 (e.g., the left and right areas divided by a central axis of a dotted line in the figure) may be spliced into the front detection area 301 in front of the main body.

Since the front contour area 201 of the main body 120 is usually set as an annular area, the front detection area 301 may also need to be set as an annular area. In some embodiments, the front detection area 301 of the front laser radar 181-1 may be not annular. In some embodiments, in order to form the front detection area 301 (of the front laser radar 181-1) with the annular shape, the contour detector 180 may include the at least two front laser radars 181-1, and the first detection sub-areas of the at least two front laser radars 181-1 may be spliced into the front detection area 301 in front of the main body 120. The rear detection area 302 may be similar to the front detection area 301, which will not be repeated herein.

In some embodiments, the at least two front laser radars 181-1 may be disposed at an interval in front of the main body 120, and the front detection area 301 in front of the main body 120 may be formed. When the main body 120 slides forward along the guide rail 130, the at least two front laser radars 181-1 may slide forward along with the main body 120 to ensure that the front detection area 301 and the front contour area 201 may have a same interval. Since the two front laser radars 181-1 are disposed at the interval, the detection sub-areas of the two front laser radars 181-1 may not completely overlapped, and the detection sub-areas of the two front laser radars 181-1 may be spliced to form a larger front detection area 301. In some embodiments, the at least two rear laser radars 181-2 may be disposed at an interval behind the main body 120 and the rear detection area 302 behind the main body 120 may be formed. The arrangement and effect of the rear laser radar 181-2 may be similar to those of the front laser radar 181-1, which can be found in the relevant descriptions above.

In some embodiments, two front laser radars 181-1 of the at least two front laser radars 181-1 may be located on a left side and a right side of the main body 120, respectively, or located on an upper side and a lower side of the main body 120, respectively. In some embodiments, two rear laser radars 181-2 of the at least two rear laser radars 181-2 may be located on the left side and the right side of the main body 120, respectively, or located on the upper side and the lower side of the main body 120, respectively. In some embodiments, the at least two front laser radars 181-1 may be symmetrically disposed in front of the main body 120 in the up-and-down direction or the left-and-right direction. In some embodiments, the at least two rear laser radars 181-2 may be symmetrically disposed behind the main body 120 in the up-and-down direction or the left-and-right direction.

Figure 9:
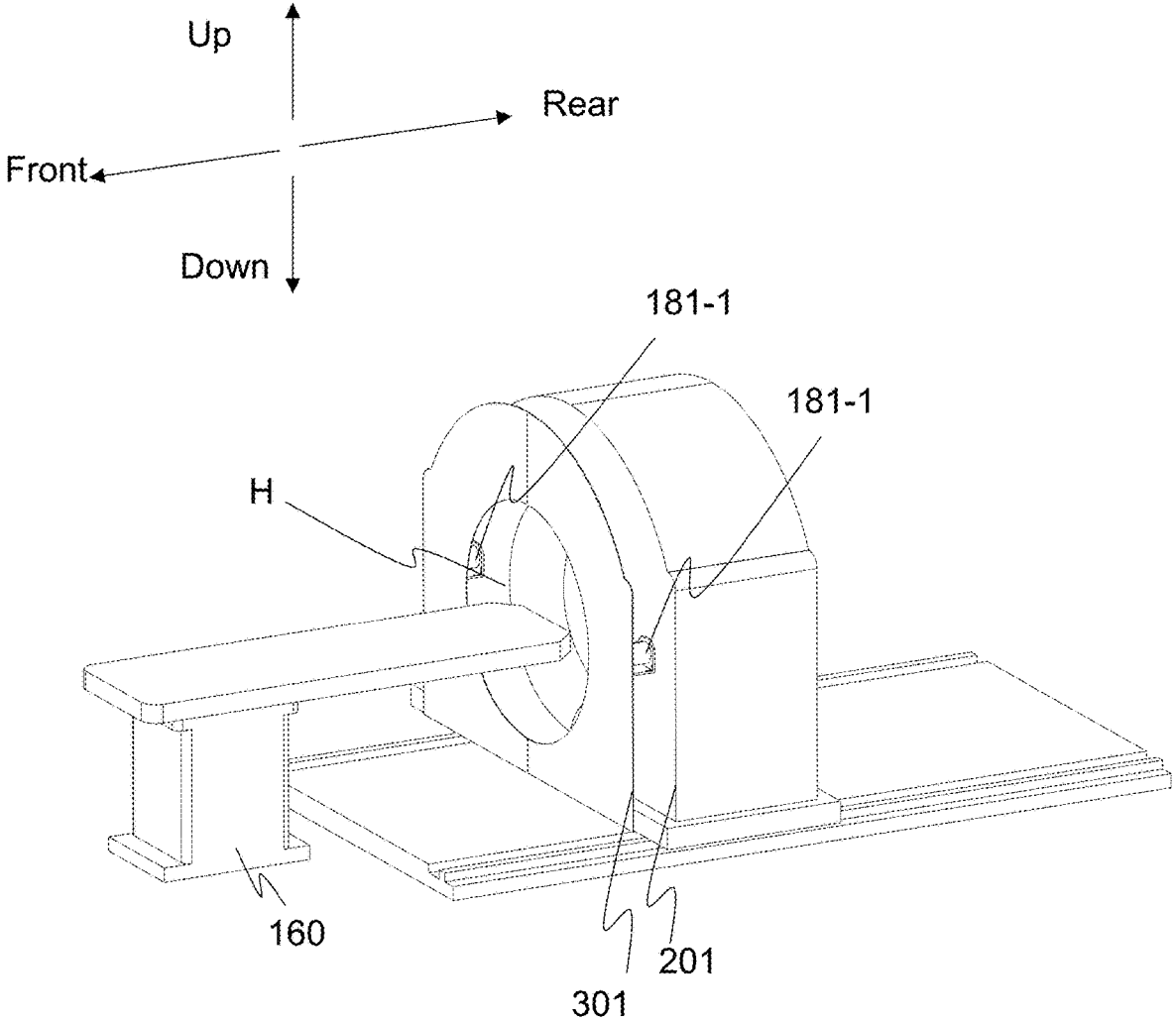
FIG. 9 is a schematic diagram illustrating obstacle avoidance detection of a mobile medical device according to other embodiments of the present disclosure.
Figure 10:
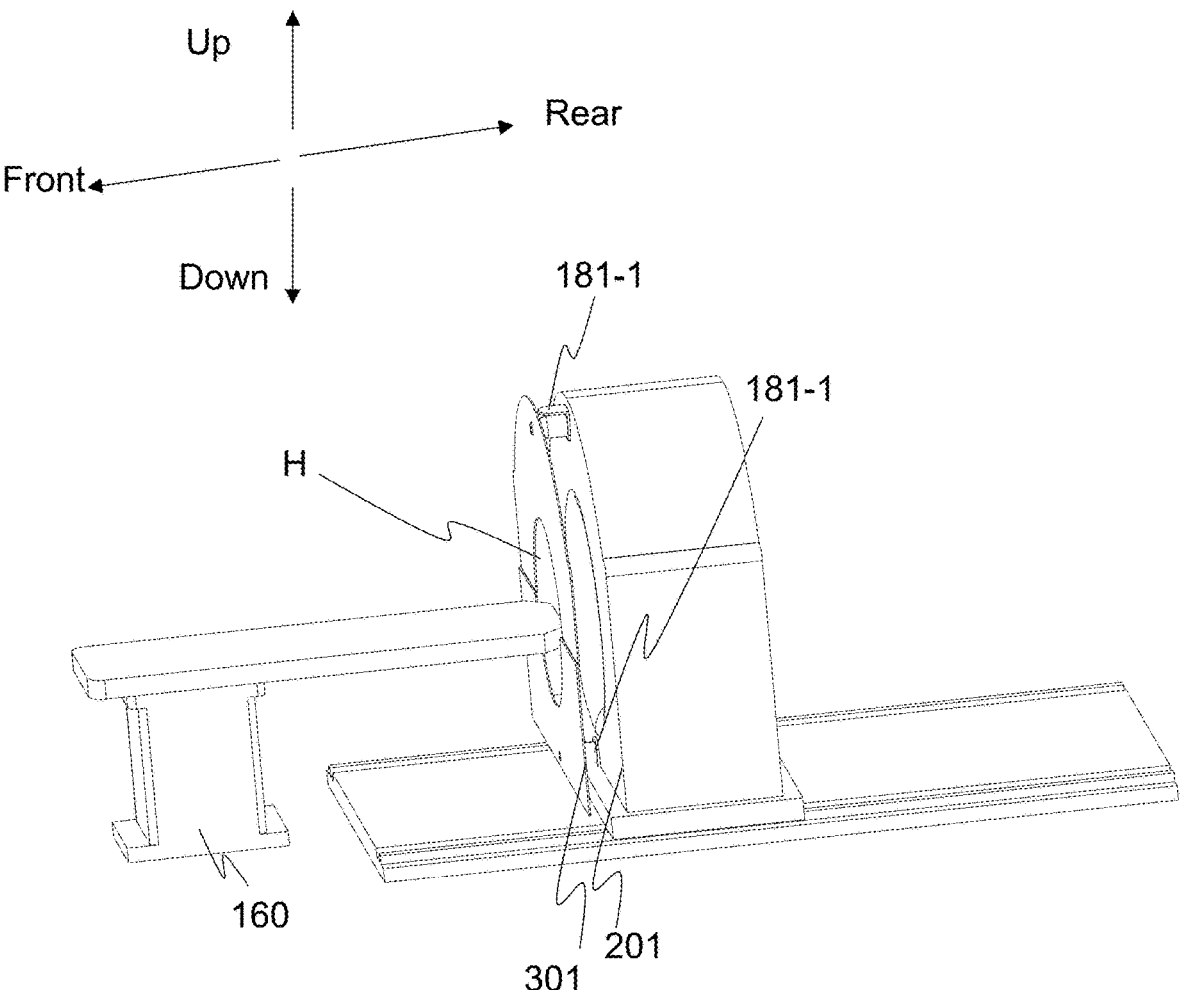
FIG. 10 is a schematic diagram illustrating obstacle avoidance detection of a mobile medical device according to other embodiments of the present disclosure.

It may be understood that since the principle of the forming of the front detection area 301 of the front laser radar 181-1 is similar to that of the rear detection area 302 of the rear laser radar 181-2, in order to simplify the description, the forming of the front detection area 301 of the front laser radar 181-1 may be described as an example below. For example, as shown in FIG. 9, the two front laser radars 181-1 may be symmetrically disposed in front of the gantry 121 in the left-and-right direction to form two first detection sub-areas in the left-and-right direction, respectively, and the two first detection sub-areas may be spliced into the front detection area 301 corresponding to the front contour area 201, which may facilitate the detection of the outer contour of the gantry 121 and the avoidance of the scanning hole H, so that the patient lying on the bed 160 can enter and exit the scanning hole H smoothly and an colliding injury to the patient can be avoided. As another example, as shown in FIG. 10, the two front laser radars 181-1 may be symmetrically disposed in front of the gantry 121 in the up-and-down direction to form two first detection sub-areas in the up-and-down direction and the two first detection sub-areas may be spliced into the front detection area 301 corresponding to the front contour area 201. By disposing the two front laser radars 181-1 symmetrically (e.g., symmetrically in the up-and-down direction or the left-and-right direction), the detection sub-areas of the two front laser radars 181-1 with similar shapes may be spliced into the front inspection area 301 conveniently. For example, if the two front laser radars 181-1 are disposed symmetrically in the left-and-right direction, the shapes of the detection sub-areas of the two front laser radars 181-1 may be exactly the same or substantially similar. As another example, if the two front laser radars 181-1 are disposed symmetrically in the up-and-down direction, part of the edges of different detection sub-areas of the two front laser radars 181-1 may be formed based on the outer contour of the contour 200 of the main body, and part of the edge of a same detection sub-area of the two front laser radars 181-1 may be formed based on the inner contour of the contour 200 of the main body.

In the illustration of the present disclosure, it should be understood that the orientation or position relationship indicated by the terms "upper," "lower," "left," and "right," etc. is based on the orientation or position relationship shown in the figures, which is merely for the purpose of illustrating and simplifying the illustration, and not to indicate or imply that the device or element referred to needs to have a specific orientation or be constructed and operated in a specific orientation, and therefore cannot be understood as a limitation of the present disclosure.

FIG. 11 is a schematic diagram of the front detection area 301 of the two front laser radars 181-1 corresponding to FIG. 8. The front contour area 201 is a two-dimensional plane and the front laser radar 181-1 is a two-dimensional laser radar. The front laser radar 181-1 may emit laser pulses (e.g., indicated by the dotted arrows in FIG. 11) at a certain angular interval to each direction within a scanning angle, so as to form the front detection area 301 corresponding to the contour 200 of the main body.

In some embodiments, due to the existence of the scanning hole H, the front detection area 301 formed by the two front laser radars 181-1 may have a detection blind area (e.g., the K area in FIG. 11). In some embodiments, in order to avoid or reduce the detection blind area, a count of front laser radars 181-1 may be further increased. For example, a front laser radar 181-1 may be disposed above the gantry 121 of the main body 120 to form a more complete front detection area 301 corresponding to the contour 200 of the main body.

Figure 12:
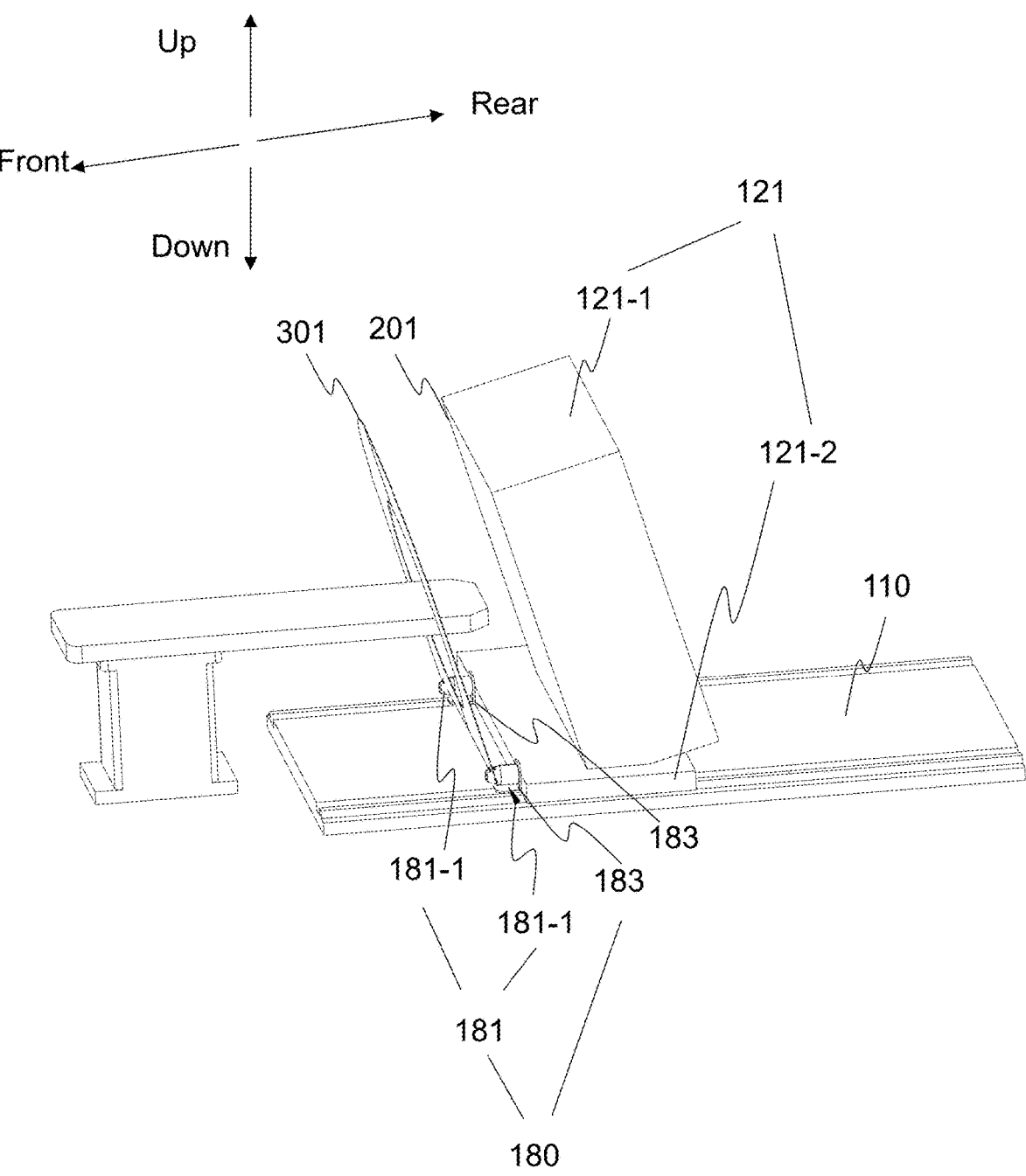
FIG. 12 is a schematic diagram illustrating obstacle avoidance detection when the mobile medical device performs oblique scanning according to some embodiments of the present disclosure.

In some embodiments, when the main body 120 performs oblique scanning on the patient according to different protocols, the main body 120 may be tilted relative to the base 110 and the detection area 300 of the laser radar 181 may also need to be tilted accordingly, so as to ensure that there is a certain gap in the moving direction between the detection area 300 and the main body 120, and the detection area 300 covers the projection of the contour 200 of the main body on the detection area 300 along the moving direction. For example, as shown in FIG. 12, in order to achieve the above effects, an obstacle avoidance device may include an angle adjustment mechanism 183. The angle adjustment mechanism 183 may adjust a tilt angle of the front laser radar 181-1 based on a tilt angle of the main body 120 to ensure that there is a certain gap in the moving direction between the front detection area 301 and the main body 120, and the front detection area 301 covers the projection of the front contour area 201 on the front detection area 301 along the moving direction.

Figure 13:
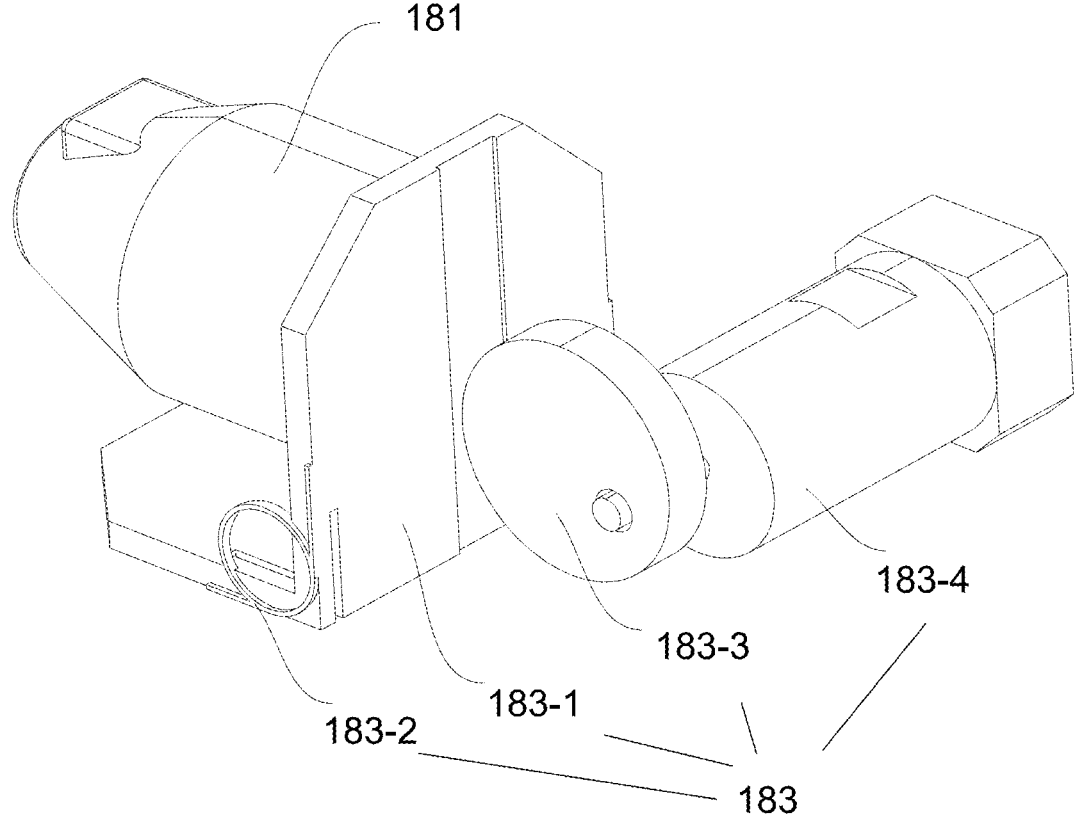
FIG. 13 is a three-dimensional schematic diagram illustrating an angle adjustment mechanism of a mobile medical device according to some embodiments of the present disclosure.
Figure 14:
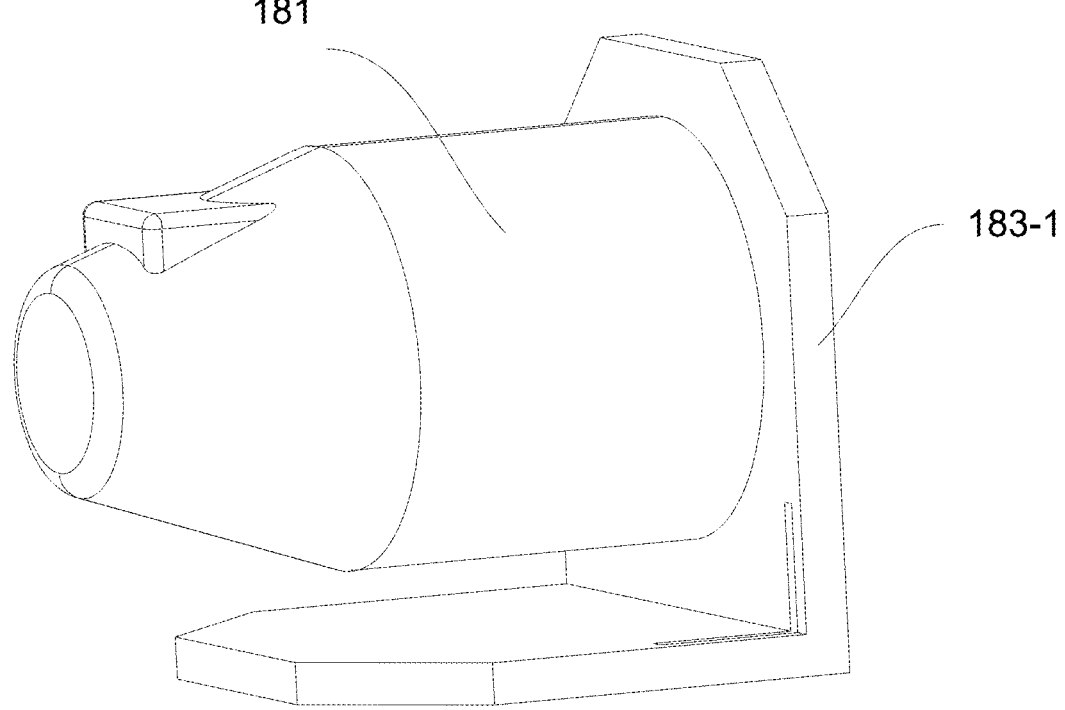
FIG. 14 is a schematic diagram illustrating an installation structure of a laser radar of the mobile medical device according to some embodiments of the present disclosure.

In some embodiments, as shown in FIG. 12, FIG. 13, and FIG. 14, the main body 120 may include a sliding table 121-2 slidably mounted on the guide rail 130. The gantry 121 may be disposed on the sliding table 121-2. The angle adjustment mechanism 183 may include a mounting base 183-1 rotatably disposed on the sliding table 121-2, a torsion spring 183-2 disposed between the mounting base 183-1 and the sliding table 121-2, an eccentric wheel 183-3 against the mounting base 183-1, and a third driving mechanism 183-4 drivably connected to the eccentric wheel 183-3. The laser radar 181 may be mounted on the mounting base 183-1. When the third driving mechanism 183-4 drives the eccentric wheel 183-3 to rotate, the mounting base 183-1 may be biased by the eccentric wheel 183-3 to rotate to a required tilt angle relative to the sliding table 121-2, so that there may be a certain gap in the moving direction between the front detection area 301 formed by the front laser radar 181-1 and the gantry 121. At the same time, the mounting base 183-1 may press against the eccentric wheel 183-3 under the action of the torsion spring 183-2, so that it may be ensured that the eccentric wheel 183-3 firmly biases the mounting base 183-1 to make the laser radar 181 rotate to the required tilt angle. At the same time, after the eccentric wheel 183-3 rotates to an initial position, the mounting base 183-1 may automatically return to a state before the rotation under the action of the torsion spring 183-2, thereby effectively ensuring that there is a certain gap in the moving direction between the front detection area 301 formed by the front laser radar 181-1 and the gantry 121.

In some embodiments, the third driving mechanism 183-4 may be communicatively connected to a controller (i.e., a third controller). The first controller, the second controller, and the third controller may be a same controller or different controllers. The third controller may be a part of the processor 140, or the third controller and the processor 140 may be two independent components. The third controller may be used to control the third driving mechanism 183-4 to drive the eccentric wheel 183-3 to rotate to a required angle according to the tilt angle of the main body support part 121-1, so that the laser radar 181 mounted on the mounting base 183-1 may rotate synchronously to the required tilt angle, thereby ensuring that there is a certain gap in the moving direction between the front detection area 301 formed by the front laser radar 181-1 and the gantry 121.

In some embodiments, the third driving mechanism may be directly connected to the mounting base or the third driving mechanism may be indirectly connected to the mounting base through a transmission mechanism such as a timing belt, so that the angle adjustment mechanism 183 may make the laser radar mounted on the mounting base rotate synchronously to the required tilt angle, which will not be repeated herein.

In some embodiments, the contour detector (180) may be disposed on the main body 120 and the contour detector (180) may be driven by the main body 120 to tilt and rotate synchronously so that a tilt angle of the main body 120 may be the same as the tilt angle of the front laser radar 181-1 and/or the rear laser radar 181-2. At this time, there may be no need to set the angle adjustment mechanism 183 and it may be ensured that there is a certain gap in the moving direction between the front detection area 301 of the front laser radar 181-1 and the gantry 121.

In some embodiments, in addition to implementing the obstacle avoidance function through contour detection by means of laser radar scanning, the contour detector 180 may perform contour detection through the visual camera 182. The required obstacle avoidance function may also be achieved.

In some embodiments, the contour detector 180 may include the visual camera 182. A visual detection area of the visual camera 182 may cover a moving area of the main body 120.

Figure 15:
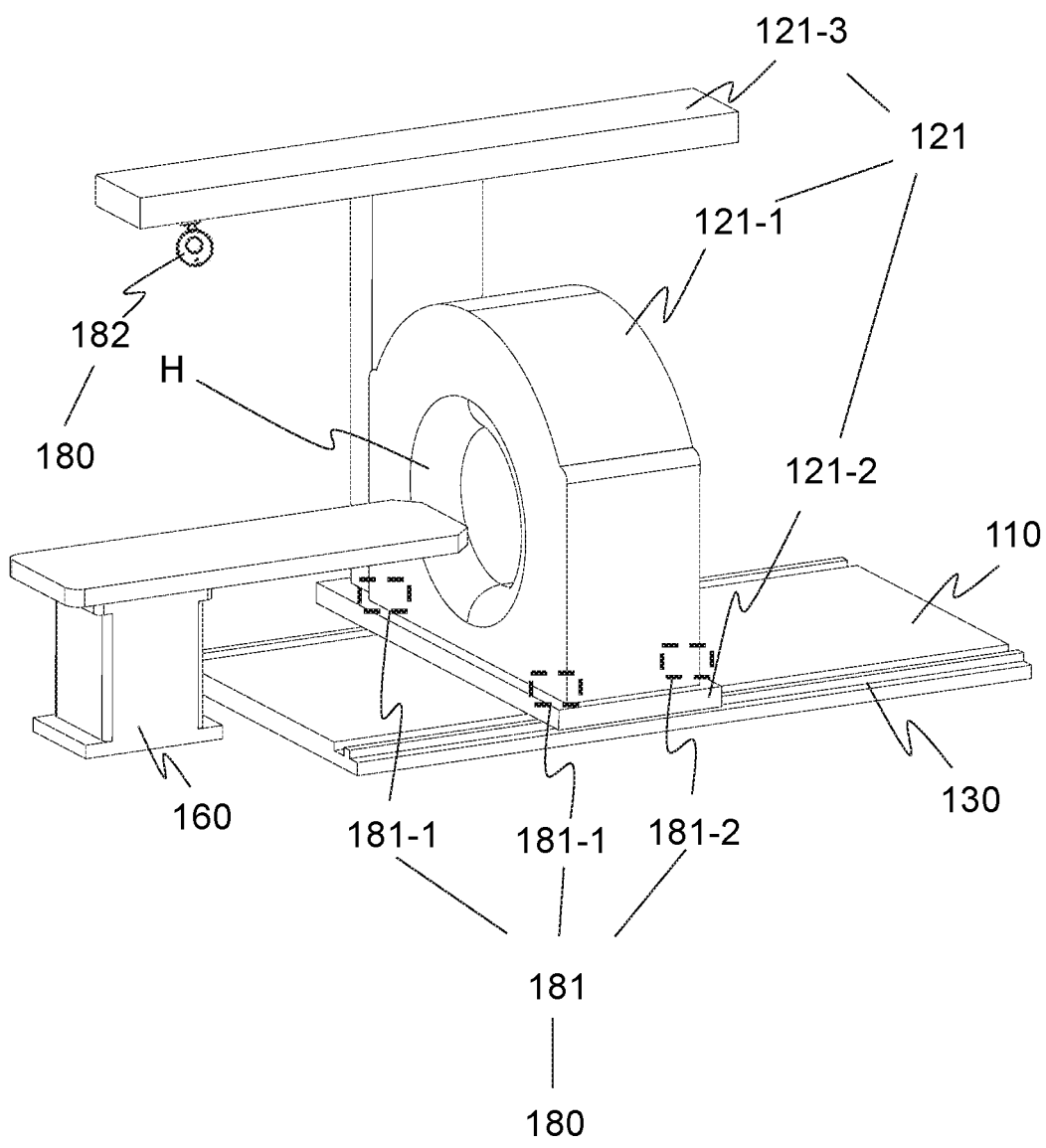
FIG. 15 is a schematic diagram illustrating obstacle avoidance detection of a mobile medical device according to other embodiments of the present disclosure; and In the figure: 110, base, 120, main body, 121, gantry, 121-1, main body support part, 121-2, sliding table, 121-3, column, 130, guide rail, 140, processor, 150, network, 160, bed body, 171, first connection terminal, 172, second connection terminal, 173, in-position detection mechanism, 174, electrical conductor, 175, power-taking device, 180, contour detector, 181, laser radar, 181-1, front laser radar, 181-2, rear laser radar, 182, visual camera, 183, angle adjustment mechanism, 183-1, mounting base, 183-2, torsion spring, 183-3, eccentric wheel, 183-4, third driving mechanism, 190, driving power supply, 200, contour of the main body, 201, front contour area, 202, rear contour area, 300, detection area, 301, front detection area, 302, rear detection area.

In some embodiments, as shown in FIG. 15, the visual camera 182 may be disposed on the column 121-3 to be located obliquely above the main body 120, so that visual inspection may be performed obliquely above the main body support part 121-1, thereby avoiding visual obstruction and performing obstacle avoidance detection effectively. In other embodiments, the visual camera 182 may be disposed at other positions, for example, various positions in the operating room where the mobile medical device is placed.

In some embodiments, a three-dimensional model of the moving area of the main body 120 may be constructed based on image data collected by the visual camera 182 and obstacle avoidance detection may be performed based on the three-dimensional model. The three-dimensional model may include a three-dimensional model of a patient, medical personnel, a medical diagnosis auxiliary device, etc. included in the moving area of the main body 120.

The visual camera 182 refers to a device for collecting the image data. For example, the visual camera may include a structured light depth camera, a time-of-flight depth camera, a binocular stereo camera, etc. In some embodiments, the visual camera 182 may be the binocular stereo camera (e.g., a binocular camera). The binocular camera may include a projector and two detectors. The projector may project a certain pattern of structured light (e.g., infrared light) on a surface of an object in the space where the moving area of the main body 120 is located and the structured light may be received by the detectors after being reflected by the surface of the object in the space where the moving area of the main body 120 is located, so that the image data modulated by a shape pf the surface of the object in the space where the movement area of the main body 120 is located may be obtained. The structured light emitted by the projector may include stripe structured light, point structured light, checkerboard structured light, or any other form of structured light. In some embodiments, the camera of the visual camera 182 may include merely one projector and one detector. In some embodiments, the camera of the visual camera 182 may include one projector and two detectors. In some embodiments, the visual camera 182 may also include other types of depth cameras.

The image data refers to data (e.g., a position feature and a shape feature of each object in the space where the movement area of the main body 120 is located) that reflects the condition of each object in the space where the movement area of the main body 120 is located. In some embodiments, the image data may include a dataset (e.g., three-dimensional spatial information of points of the surface of each object in the space where the moving area of the main body 120 is located) of various objects in the space where the moving area of the main body 120 is located. In some embodiments, the image data may include depth image data, red-green-blue (RGB) image data, three-dimensional point cloud data, etc. In some embodiments, the image data may include image data of the patient, the medical personnel, the medical diagnosis auxiliary device, etc., included in the moving area of the main body 120.

In some embodiments, the processor 140 may construct the three-dimensional model of the moving area of the main body 120 through a technology such as a point cloud three-dimensional reconstruction technology, a binocular vision reconstruction technology, etc. In some embodiments, the processor 140 may construct the three-dimensional model of the moving area of the main body 120 using other technologies, which is not limited herein.

In some embodiments, the visual camera 182 may collect the image data of the space where the moving area of the main body 120 is located in real time, update the data, and update the three-dimensional model in real time for obstacle avoidance detection. For example, when the processor 140 detects that in the determined three-dimensional model, a distance between the main body 120 and the obstacle is smaller than a preset threshold (e.g., 0.2 m, 0.5 m, 0.8 m, etc.), the processor 140 may control the main body 120 to brake to avoid the obstacle.

The image data may be collected by the visual camera 182 in real time, a change of the distance between the main body 120 and the obstacle in real space may be perceived in real time, so as to realize accurate obstacle avoidance.

In some embodiments, the contour detector 180 may be a combination of the three-dimensional laser radar or the two-dimensional laser radar and the distance sensor, or the visual camera 182. The contour detector 180 may detect the distance between the main body 120 and the obstacle. The controller (e.g., the second controller) of the obstacle avoidance device may be configured to: detect the distance between the main body 120 and the obstacle; in response to a determination that the distance is smaller than or equal to a first preset distance, adopt a first obstacle avoidance strategy; or in response to a determination that the distance is greater than the first preset distance but smaller than or equal to a second preset distance, adopt a second obstacle avoidance strategy different from the first obstacle avoidance strategy. The second preset distance may be greater than the first preset distance (e.g., the first preset distance may be 0.5 m and the second preset distance may be 2 m).

In some embodiments, the first obstacle avoidance strategy may include controlling the main body 120 to brake and stop. The second obstacle avoidance strategy may include controlling the main body 120 to decelerate and/or controlling the contour detector to shorten a detection time interval. The detection time interval may be a time interval between two detections of obstacle by the contour detector 180. For example, if the contour detector 180 is the visual camera 182, the detection time interval may be a time interval for updating the three-dimensional model. In some embodiments, the second obstacle avoidance strategy may also include reminding the user to pay attention to the obstacle through voice, light, etc.

Different obstacle avoidance strategies may be implemented based on different distances, so that when the distance between the main body 120 and the obstacle reaches a warning distance (e.g., a distance greater than the first preset distance but smaller than or equal to the second preset distance), the distance can be prevented from being shortened by reducing a speed, increasing a detection frequency, reminding the operator, etc. If the distance is still further shortened to a dangerous distance (e.g., smaller than or equal to the first preset distance), the main body 120 may be braked and stopped to prevent friction and collision between the main body 120 and the obstacle.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A mobile medical device, comprising a main body and an obstacle avoidance device, wherein a gantry of the main body is capable of moving;

the obstacle avoidance device includes a contour detector, and the contour detector is configured to detect an obstacle in a moving direction of the main body according to a contour of the main body;

the contour detector includes a front laser radar forming a detection area corresponding to the contour of the main body in front of the main body; and

the contour detector further includes a rear laser radar forming a detection area corresponding to the contour of the main body behind the main body, the detection area formed by the front laser radar and the detection area formed by the rear laser radar are equal to or larger than the contour of the main body.

2. The mobile medical device of claim 1, further comprising a first transmission component and a second transmission component, wherein the second transmission component is disposed on the gantry; and the first transmission component and the second transmission component are capable of being connected to transmit energy and/or a signal for the mobile medical device.

3. The mobile medical device of claim 2, wherein the first transmission component includes a first connection terminal, the second transmission component includes a second connection terminal, and the first connection terminal and the second connection terminal coordinate to transmit the energy and/or the signal.

4. The mobile medical device of claim 3, wherein the first connection terminal is movably disposed, the first connection terminal is connected to a first driving mechanism, and the first driving mechanism is configured to drive the first connection terminal to move.

5. The mobile medical device of claim 3, wherein a driving power supply is disposed on the gantry;

the mobile medical device includes a second driving mechanism, and the second driving mechanism is configured to drive the gantry to move;

the driving power supply is connected to the second driving mechanism;

in a process of moving the gantry to a target position, the gantry is provided with the energy by the driving power supply;

when the gantry moves to the target position to enable the first connection terminal to contact the second connection terminal, the second connection terminal on the gantry is automatically aligned and plugged with the first connection terminal fixed on a base, so that the first connection terminal and the second connection terminal are synchronously charge the driving power supply carried by the gantry.

6. The mobile medical device of claim 2, wherein the first transmission component includes an electrical conductor extending along a movement direction of the gantry of the main body; and the second transmission component includes a power-taking device.

7. The mobile medical device of claim 1, further comprising a controller communicatively connected to the contour detector and the main body, wherein the controller is configured to:

in response to that the contour detector detects that an obstacle exists in the moving direction of the main body, control the main body to brake to avoid the obstacle.

8. The mobile medical device of claim 1, wherein the contour detector is disposed at a position spaced apart from the gantry; and there is a gap in the moving direction between the detection area and the main body.

9. The mobile medical device of claim 8, wherein the contour detector includes at least two front laser radars, each of the at least two front laser radars forms a first detection sub-area in front of the main body, and the first detection sub-areas formed by the at least two front laser radars are spliced into the detection area in front of the main body; and/or the contour detector includes at least two rear laser radars, each of the at least two rear laser radars forms a second detection sub-area behind the main body, and the second detection sub-areas formed by the at least two rear laser radars are spliced into the detection area behind the main body.

10. The mobile medical device of claim 9, wherein two front laser radars of the at least two front laser radars are located on a left side and a right side of the main body, respectively, or located on an upper side and a lower side of the main body, respectively; and/or two rear laser radars of the at least two rear laser radars are located on the left side and the right side of the main body, respectively, or located on the upper side and the lower side of the main body, respectively.

11. The mobile medical device of claim 1, wherein the obstacle avoidance device includes an angle adjustment mechanism, wherein the angle adjustment mechanism adjusts a tilt angle of the front laser radar and/or the rear laser radar based on a tilt angle of the main body.

12. The mobile medical device of claim 11, wherein the main body includes a sliding table slidably mounted on the guide rail, the gantry is disposed on the sliding table;

the angle adjustment mechanism includes a mounting base rotatably disposed on the sliding table, a torsion spring disposed between the mounting base and the sliding table, the eccentric wheel against the mounting base, and a third driving mechanism drivably connected to the eccentric wheel;

the front laser radar and/or the rear laser radar are mounted on the mounting base; and the third driving mechanism drives the eccentric wheel to rotate and the mounting base is biased by the eccentric wheel to adjust the tilt angle of the front laser radar and/or the rear laser radar mounted on the mounting base.

13. The mobile medical device of claim 1, wherein the contour detector is disposed on the main body and the contour detector is driven by the main body to tilt and rotate synchronously with the main body so that a tilt angle of the main body is the same as a tilt angle of the front laser radar and/or the rear laser radar.

14. The mobile medical device of claim 1, wherein the front laser radar and the rear laser radar include a two-dimensional laser radar or a three-dimensional laser radar.

15. The mobile medical device of claim 1, wherein the contour detector includes a visual camera; and a visual detection area of the visual camera covers a moving area of the main body.

16. The mobile medical device of claim 7, wherein the contour detector detects a distance between the main body and the obstacle; and the controller is configured to:

in response to a determination that the distance is smaller than or equal to a first preset distance, adopt a first obstacle avoidance strategy; or in response to a determination that the distance is greater than the first preset distance but smaller than or equal to a second preset distance, adopt a second obstacle avoidance strategy different from the first obstacle avoidance strategy, wherein the second preset distance is greater than the first preset distance.

17. The mobile medical device of claim 16, wherein:

the first obstacle avoidance strategy includes controlling the main body to brake and stop; and the second obstacle avoidance strategy includes controlling the main body to decelerate and/or controlling the contour detector to shorten a detection time interval.

18. The mobile medical device of claim 11, wherein the angle adjustment mechanism includes an eccentric wheel, and the eccentric wheel is configured to rotate to adjust a tilt angle of the contour detector.

19. The mobile medical device of claim 1, wherein a shape of the detection area formed by the front laser radar and a shape of the detection area formed by the rear laser radar are identical to the contour of the main body.

20. The mobile medical device of claim 1, wherein the detection area formed by the front laser radar and the detection area formed by the rear laser radar are annular.

* * * * *